United States Patent [19]

Maurer et al.

[11] Patent Number: 5,310,722

[45] Date of Patent: May 10, 1994

[54] SYNERGISTIC COMPOSITION COMPRISING A SULFONYLUREA AND A THIADIAZOLO[3,4-A]PYRIDAZINE AND METHOD OF SELECTIVE WEED CONTROL

[75] Inventors: Willy Maurer, Riehen; Urs Hofer, Rheinfelden, both of Switzerland

[73] Assignee: Ciba-Geigy Corporation, Ardsley, N.Y.

[21] Appl. No.: 931,120

[22] Filed: Aug. 17, 1992

Related U.S. Application Data

[63] Continuation of Ser. No. 753,490, Sep. 3, 1991, abandoned.

[30] Foreign Application Priority Data

Sep. 6, 1990 [CH] Switzerland .................. 2890/90

[51] Int. Cl.[5] .................. A01N 43/48; A01N 43/64; A01N 43/82; A01N 47/36
[52] U.S. Cl. .................. 504/134; 504/137
[58] Field of Search .................. 71/90, 93; 504/134, 504/137; A01N 43/48, 43/64, 43/82, 47/36

[56] References Cited

U.S. PATENT DOCUMENTS

| | | | |
|---|---|---|---|
| 4,443,243 | 4/1984 | Fory et al. | 71/93 |
| 4,478,635 | 10/1984 | Meyer et al. | 71/93 |
| 4,515,626 | 5/1985 | Szczepanski | 71/93 |
| 4,537,618 | 8/1985 | Schurter et al. | 71/92 |
| 4,545,811 | 10/1985 | Meyer et al. | 71/93 |
| 4,549,898 | 10/1985 | Böhner et al. | 71/90 |
| 4,579,584 | 4/1986 | Meyer et al. | 71/93 |
| 4,618,363 | 10/1986 | Gass et al. | 71/90 |
| 4,759,791 | 7/1988 | Föry et al. | 71/91 |

(List continued on next page.)

FOREIGN PATENT DOCUMENTS

| | | |
|---|---|---|
| 0603232 | 11/1990 | Australia . |
| 0044807 | 1/1982 | European Pat. Off. . |
| 0044808 | 1/1982 | European Pat. Off. . |
| 0044809 | 1/1982 | European Pat. Off. . |

(List continued on next page.)

*Primary Examiner*—Richard L. Raymond
*Assistant Examiner*—S. Mark Clardy
*Attorney, Agent, or Firm*—Edward McC. Roberts

[57] ABSTRACT

The present invention relates to a synergistic composition comprising a herbicidally active gulfonylurea of formula I

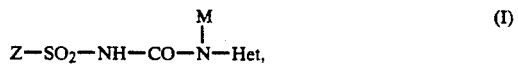

wherein
Z is a substituted phenyl, thiophenyl, benzyl, pyridinyl, pyrazinyl, hetero-fused phenyl, or alkylsulfonylamino radical;
M is hydrogen; or $C_1$-$C_4$alkyl; and Het is a substituted five- or six-membered heterocycle having 2 or 3 nitrogen atoms, and a synergistically effective amount of a 5,6,7,8-tetrahydro-1-H,3H-(1,3,4)-thiadiazolo[3,4-a]-pyridazine or 7,8-dihydro-1-H,3H-(1,3,4)-thiadiazolo[3,4-a]pyridazine of formula II

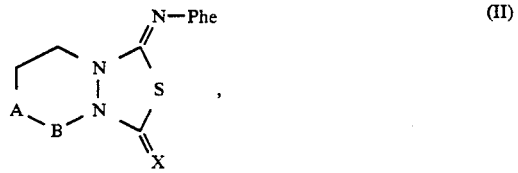

wherein
X is oxygen; or sulfur;
A—B is —$CH_2$—$CH_2$—; or —CH=CH—; and
Phe is a substituted phenyl radical.

The composition according to the invention is suitable for selective weed control in crops of useful plants, especially in cereals, maize, rice or soybeans. The invention relates also to a method of controlling weeds in crops of useful plants, especially in cereals, maize, rice or soybeans, and to the use of the novel composition.

16 Claims, No Drawings

U.S. PATENT DOCUMENTS

| | | | |
|---|---|---|---|
| 4,780,125 | 10/1988 | Meyer et al. | 71/93 |
| 4,795,486 | 1/1989 | Böhner et al. | 71/93 |
| 4,816,063 | 3/1989 | Yamaguchi et al. | 71/90 |
| 4,885,023 | 12/1989 | Yamaguchi et al. | 71/90 |
| 4,927,448 | 5/1990 | Yamaguchi et al. | 71/90 |
| 4,927,450 | 5/1990 | Föry et al. | 71/91 |
| 5,039,331 | 8/1991 | Satow et al. | 71/90 |

FOREIGN PATENT DOCUMENTS

| | | |
|---|---|---|
| 0096003 | 12/1983 | European Pat. Off. . |
| 0103537 | 3/1984 | European Pat. Off. . |
| 0120814 | 10/1984 | European Pat. Off. . |
| 0126711 | 11/1984 | European Pat. Off. . |
| 0169815 | 1/1986 | European Pat. Off. . |
| 0298901 | 1/1989 | European Pat. Off. . |
| 0304920 | 3/1989 | European Pat. Off. . |

SYNERGISTIC COMPOSITION COMPRISING A SULFONYLUREA AND A THIADIAZOLO[3,4-A]PYRIDAZINE AND METHOD OF SELECTIVE WEED CONTROL

This application is a continuation of application Ser. No. 07/753,490, filed Sep. 3, 1991 now abandoned.

The present invention relates to a synergistic composition comprising a herbicidal active ingredient combination. The composition according to the invention is suitable for selective weed control in crops of useful plants, especially in cereals, maize, rice or soybeans.

The invention relates also to a method of controlling weeds in crops of useful plants, especially in cereals, maize, rice or soybeans, and to the use of the novel composition.

The composition according to the invention comprises a mixture of two active ingredient components that are known per se. The first active ingredient is a herbicidally active sulfonylurea of the general formula I

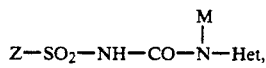
(I)

wherein

Z is a substituted phenyl, thiophenyl, benzyl, pyridinyl, pyrazinyl, hetero-fused phenyl, or alkylsulfonylamino radical;

M is hydrogen; or $C_1$–$C_4$alkyl; and

Het is a substituted five- or six-membered heterocycle having 2 or 3 nitrogen atoms, and the agochemically acceptable salts thereof.

Herbicidally active sulfonylureas of formula I are described, for example, in the following literature references: DE-A-2 715 786, EP-A-0 004 163, EP-A-0 007 687, EP-A-0 013 480, EP-A-0 023 141, EP-A-0 023 422, EP-A-0 030 139, EP-A-0 030 142, EP-A-0 035 893, EP-A-0 044 209, EP-A-0 044 210, EP-A-0 044 21 1, EP-A-0 044 212, EP-A-0 044 213, EP-A-0 044 807, EP-A-0 044 808, EP-A-0 044 809, EP-A-0 048 143, EP-A-0 051 466, EP-A-0 057 456, EP-A-0 070 802, EP-A-0 072 347, EP-A-0 073 562, EP-A-0 079 683, EP-A-0 082 108, EP-A-0 083 975, EP-A-0 084 020, EP-A-0 084 224, EP-A-0 085 028, EP-A-0 085 476, EP-A-0 087 780, EP-A-0 095 925, EP-A-0 096 002, EP-A-0 096 003, EP-A-0 096 593, EP-A-0 097 122, EP-A-0 102 925, EP-A-0 103 537, EP-A-0 107 979, EP-A-0 108 708, EP-A-0 11 7 014, EP-A-0 120 814, EP-A-0 126 711, EP-A-0 169 815, EP-A-0 176 304, EP-A-0 184 385, EP-A-0 206 995, EP-A-0 237 292, EP-A-0 238 070, EP-A-0 262 096, EP-A-0 273 860, EP-A-0 327 251, EP-A-0 336 587, EP-A-0 342 456, US-4 774 337 and European Patent Application No. 90 810 392.2.

Some of the sulfonylureas that can be used according to the invention are also already commercially available.

The second active ingredient is a 5,6,7,8-tetrahydro-1H,3H-(1,3,4)-thiadiazolo[3,4-a]pyridazine or 7,8-dihydro- I H,3H-(1,3,4)-thiadiazolo[3,4-a]pyridazine of the general formula II

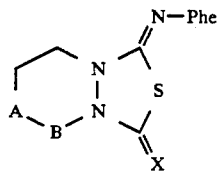
(II)

wherein

X is oxygen; or sulfur;

A—B is —CH$_2$—CH$_2$—; or —CH=CH—; and

Phe is a substituted phenyl radical.

The compounds of formula 11 have been described in the prior published European Patent Applications EP-A-0 238 71 1, EP-A-0 273 417 and EP-A-0 304 920 as herbicidally active compounds. The compounds of formula II are described in more detail especially in those publications and also in the U.S. Pat. No. 4,816,063 and U.S. Pat. No. 4,885,023 corresponding to EP-A-0 238 71 1. The above-mentioned publications, especially EP-A-0 238 71 1, EP-A-0 273 417, EP-A-0 304 920, EP-A-0 312 064, U.S. Pat. No. 4,816,063 and US 4 885 023, are mentioned as references.

It has now been found that the sulfonylureas of formula I can be combined in an advantageous manner with the herbicidally active 5,6,7,8-tetrahydro-1H,3H-(1,3,4)-thiadiazolo[3,4-a]pyridazines or 7,8-dihydro-1H,3H-(1,3,4)-thiadiazolo-[3,4-a]pyridazines of the general formula II disclosed in the above-mentioned publications. The combination of the compounds of the two groups of active ingredients of formulae I and II exhibits a synergistic (superadditive) herbicidal action that is superior to the purely additive action of the particular class of compounds at a given rate of application.

Especially suitable as the alkylsulfonylamino radical Z is the radical of the formula

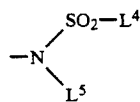

wherein $L^4$ and $L^5$ are as defined below.

The present Application relates especially to the combination of a sulfonylurea of formula

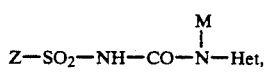
(I)

wherein

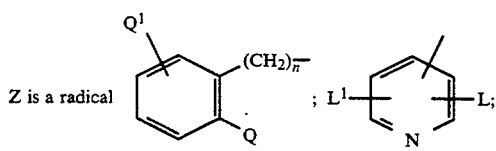

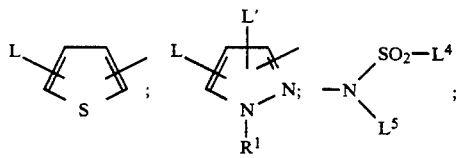

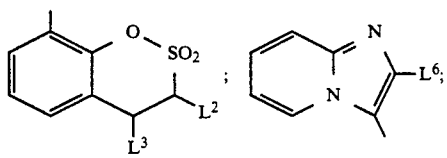

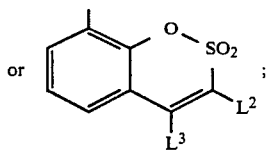

Het is a radical 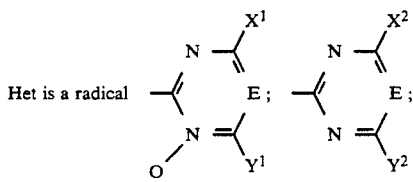

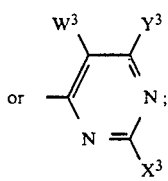

M is hydrogen; or $C_1$-$C_4$alkyl;

Q is halogen; nitro; $C_1$-$C_6$alkyl; $C_1$-$C_6$haloalkyl; $C_2$-$C_6$alkenyl; $C_2$-$C_6$haloalkenyl; $C_2$-$C_6$alkynyl; $C_3$-$C_6$haloalkynyl; —$NH_2$; —NH—($C_1$-$C_4$alkyl); —N($C_1$-$C_4$alkyl)$_2$; —$SO_2$N—($C_1$-$C_{alkyl}$)$_2$; —$SO_2$NH($C_1$-$C_4$alkyl); —COOR$_2$; —COOR'; —(A)—R'; —(A)—R$_2$; phenyl; phenoxy; $C_1$-$C_5$alkylphenyl; halophenyl; or halophenoxy;

$Q^1$ is hydrogen; nitro; $C_1$-$C_4$alkyl; halogen; $C_1$-$C_4$alkoxy; $C_1$-$C_4$haloalkyl; N($C_1$-$C_4$alkyl)$_2$; $C_1$-$C_4$alkylamino; $C_1$-$C_4$haloalkylthio; $C_1$-$C_4$haloalkoxy; $C_1$-$C_4$-alkoxy-$C_1$-$C_4$alkoxy; $C_2$-$C_4$alkenyl; $C_2$-$C_4$alkynyl; CN; or $C_2$-$C_4$haloalkenyl;

n is 0; or 1;

$R^1$ is hydrogen; $C_1$-$C_4$alkyl; or pyridyl;

A is oxygen; sulfur; —SO—; —$SO_2$—; or —O—$SO_2$—;

$R^2$ is $C_1$-$C_5$alkyl; $C_2$-$C_6$akenyl; $C_3$-$C_6$akynyl; $C_1$-$C_5$-haloalkyl; $C_1$-$C_4$alkoxy-$C_1$-$C_4$alkyl; $C_2$-$C_5$-haloalkenyl; or $C_2$-$C_5$haloalkynyl;

R' is oxetan-3-yl; or thietan-3-yl;

L is halogen; nitro; $C_1$-$C_5$alkyl; —A—R$_2$; COOR$_2$; —CO—$NH_2$; —CO—NHC$_1$-C$_4$ alkyl; or —CO—N($C_1$-$C_4$alkyl)$_2$;

L' is hydrogen; or chlorine;

$L^1$ is hydrogen; nitro; $C_1$-$C_4$alkyl; halogen; $C_1$-$C_4$alkoxy; $C_1$-$C_4$haloalkyl; or $C_1$-$C_6$haloalkoxy;

$L^2$ is hydrogen; or $C_1$-$C_4$alkyl;

$L^3$ is hydrogen; or $C_1$-$C_4$alkyl;

$L^4$ is C-$C_6$alkyl; $C_2$-$C_6$alkenyl; or $C_2$-$C_6$alkynyl;

$L^5$ is $C_1$-$C_6$alkyl; $C_2$-$C_6$alkenyl; or $C_2$-$C_6$alkynyl; or $L^4$ and $L^5$ together are a $C_2$-$C_6$alkylene bridge;

E is N; or CH;

$X^1$, $X^2$, $X^3$ and $Y^1$, each independently of the others, is hydrogen; halogen; $C_1$-$C_4$haloalkoxy; $C_1$-$C_4$-haloalkyl; $C_1$-$C_4$alkoxy; $C_1$-$C_4$alkyl; cyclopropyl; dimethylamino; methylamino; ethylamino; amino; $C_1$-$C_4$alkoxy-$C_1$-$C_4$alkyl; $C_1$-$C_4$alkoxy-$C_1$-$C_4$alkoxy; $C_1$-$C_4$haloalkylthio; $C_1$-$C_4$alkylthio; or $C_1$-$C_4$alkylthio-$C_1$-$C_4$alkyl;

$Y^2$ is hydrogen; halogen; $C_1$-$C_4$haloalkoxy; $C_1$-$C_4$-haloalkyl; $C_1$-$C_4$alkoxy; $C_1$-$C_4$alkyl; dimethylamino; methylamino; ethylamino; amino; $C_1$-$C_4$alkoxy-$C_1$-$C_4$alkyl; cyclopropyl; dimethoxymethyl; diethoxyethyl;

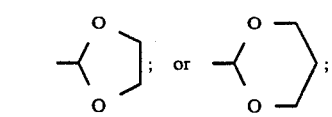

$Y^3$ is $C_1$-$C_4$alkyl; $C_1$-$C_4$alkoxy; $C_1$-$C_2$haloalkyl; or $C_1$-$C_2$haloalkoxy;

$W^3$ is hydrogen; $C_1$-$C_4$alkyl; $C_1$-$C_4$alkoxy; $C_1$-$C_2$-haloalkyl; $C_1$-$C_2$haloalkoxy; $C_1$-$C_4$alkoxycarbonyl; halogen; cyano; nitro; $C_1$-$C_4$alkylthio; $C_1$-$C_4$alkylsulfinyl; or $C_1$-$C_4$alkylsulfonyl; or $W^3$ and $Y^3$ together are a $C_2$-$C_4$alkylene bridge; or a $C_1$-$C_3$alkylene bridge interrupted once by oxygen; with a synergistically effective amount of a 5,6,7,8-tetrahydro-1H,3H-(I,3,4)-thiadiazolo-[3,4-a]pyridazine or 7,8-dihydro-1H,3H-(1,3,4)-thiadiazolo[3,4-a]pyridazine of formula II

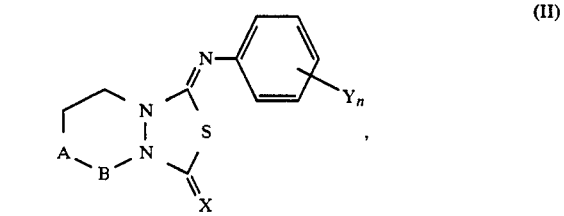

wherein

A—B is —$CH_2$—$CH_2$—; or —CH=CH—;

each Y, independently of the others, is halogen; hydroxy; $C_1$-$C_6$alkyl; $C_1$-$C_6$alkoxy; $C_1$-$C_6$haloalkoxy; $C_3$-$C_6$alkenyloxy; $C_2$-$C_6$haloalkenyloxy; $C_3$-$C_6$alkynyloxy; phenoxy; $C_5$-$C_6$cycloalkyloxy; $C_1$-$C_6$alkoxycarbonyl-$C_1$-$C_4$alkoxy; $C_1$-$C_6$alkoxycarbonyl-$C_2$-$C_4$alkenyloxy; $C_1$-$C_6$alkylthiocarbonyl-$C_1$-$C_4$alkoxy; $C_3$-$C_6$oxycarbonyl-$C_1$-$C_4$alkoxy; benzyloxycarbonyl-$C_1$-$C_4$alkoxy; trifluoromethyl; benzyloxy; chlorobenzyloxy; $C_1$-$C_6$alkylbenzyloxy; $C_2$-$C_6$alkenyl; cyano $C_1$-$C_6$alkyl; $C_1$-$C_6$alkylcarbamoyloxy; $C_1$-$C_4$alkoxy-$C_1$-$C_4$alkyl; $C_3$-$C_6$alkynyloxy-$C_1$-$C_4$alkyl; $C_3$-$C_6$alkenyloxy-$C_1$-$C_3$alkyl; unsubstituted or halo-substituted $C_5$-$C_6$cycloalkylmethoxy; $C_1$-$C_6$alkoxy-$C_1$-$C_4$alkoxy; phenethyloxy; $C_5$-$C_6$cycloalkoxycarbonyl-$C_1$-$C_4$alkoxy; pyrrolidinocarbonyl; unsubstituted or $C_1$-$C_6$alkyl-substituted phenylcarbonyl;

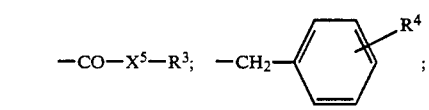

—S(O)$_p$—R$^5$; —O—CH(R$^6$)—CO—OR$^7$;
—N=C(CH$_3$)— R$^8$; —NHR$^9$; —S—CH(R$^{10}$)—CO—R$^{11}$; or —O—P(X$^5$)(OC$_2$H$_5$)$_2$;

$R^3$ is hydrogen; $C_1-C_6$alkyl; phenyl; $C_5-C_6$cycloalkyl; $C_1-C_6$alkoxy-$C_1-C_4$alkyl; $C_1-C_6$-alkoxycarbonyl-$C_1-C_4$alkyl; or $C_1-C_4$alkoxy-$C_1-C_4$alkoxycarbonyl-$C_1-C_4$alkyl;

$R^4$ is hydrogen; $C_1-C_6$alkoxy; $C_1-C_4$alkyl; or halogen;

$R^5$ is $C_1-C_6$alkyl; $C_2-C_6$alkenyl; or $C_2-C_6$alkynyl;

p is 0 or 2;

$R^6$ is hydrogen; or $C_1-C_6$alkyl;

$R^7$ is hydrogen; $C_1-C_6$alkyl; $C_1-C_6$alkoxy-$C_1-C_4$alkyl; tetrahydrofuryl; $C_1-C_4$alkoxy-$C_1-C_4$alkoxy-$C_1-C_4$alkyl; $C_1-C_6$alkoxycarbonyl-$C_1-C_4$alkyl; or $C_5-C_6$cycloalkyl;

$R^8$ is $C_1-C_6$alkyl; or phenyl;

$R^9$ is $C_1-C_6$alkylcarbonyl; or $C_1-C_6$alkoxycarbonyl-$C_1-C_4$alkyl;

$R^{10}$ is hydrogen; or $C_1-C_6$alkyl;

$R^{11}$ is $C_1-C_6$alkoxy; $C_5-C_6$cycloalkyloxy; 1-pyrrolidinyl; $C_3-C_6$alkenyloxy; $C_3-C_6$alkynyloxy; $C_1-C_6$alkylthio; $C_1-C_4$haloalkoxy; $C_1-C_4$alkoxycarbonyl-$C_1-C_4$alkoxy; α,α-dimethylbenzylamino; $-OC_2H_4S(O)_2-(C_1-C_6\text{alkyl})$; $-OC_2H_4S-(C_1-C_6\text{alkyl})$; $-OC_2H_4S(O)_2$-(phenyl); $-OC_2H_4S$-(phenyl);

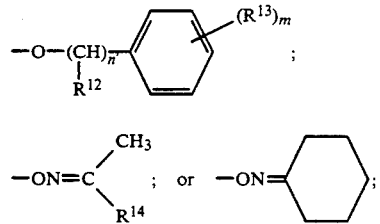

n' is 0; or 1;

$R^{12}$ is halogen; or $C_1-C_4$alkyl;

$R^{13}$ is phenyl; benzyl; or methoxy-$C_1-C_4$alkyl;

$R^{14}$ is styryl; cyano-$C_1-C_4$alkyl; tetrahydrofuran-2-yl, thienyl or pyridin-2-yl;

X is oxygen; or sulfur;

$X^5$ is oxygen; or sulfur;

m is 0; 1; 2; or 3;

and n is 0; 1; 2; or 3.

In the above definitions, halogen is to be understood as being fluorine, chlorine, bromine and iodine, preferably fluorine, chlorine and bromine.

The alkyl groups occurring in the definitions of the substituents may be straight-chained or branched and are, for example, methyl, ethyl, n-propyl, isopropyl, n-butyl, sec-butyl, isobutyl or tert-butyl. The alkyl groups occurring as or in the substituents preferably have from 1 to 3 carbon atoms.

Alkenyl is to be understood as being straight-chained or branched alkenyl, for example vinyl, allyl, methallyl, 1-methylvinyl or but-2-en-1-yl. Alkenyl radicals having a chain length of from 2 to 4 carbon atoms are preferred.

Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

The alkoxy groups occurring in the definitions of the substituents may be straight-chained or branched and are, for example, methoxy, ethoxy, propoxy, isopropoxy, n-butoxy, isobutoxy, sec-butoxy and tert-butoxy; the alkoxy groups occurring as or in the substituents preferably have 1 or 2 carbon atoms, preferably methoxy and ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy; preferably difluoromethoxy, 2-chloroethoxy and tiifluoromethoxy.

Alkylthio is, for example, methylthio, ethylthio, propylthio, isopropylthio, n-butylthio, isobutylthio, sec-butylthio or tert-butylthio, preferably methylthio and ethylthio.

Examples of alkoxyalkoxy are: methoxymethoxy, methoxyethoxy, methoxypropoxy, ethoxymethoxy, ethoxyethoxy and propoxymethoxy.

Alkynyl is to be understood as being straight-chained or branched alkynyl, for example ethynyl and but-2-yn-1-yl.

Haloalkenyl is, for example, 3,3-difluorobut-2-en-1-yl.

Haloalkynyl is, for example, 3-chlorobut-2-yn-1-yl.

Cycloalkyloxy is, for example, pentyloxy and hexyloxy.

Alkylphenyl, halophenyl and halophenoxy are to be understood as being, for example, phenyl radicals mono-, di-, tri- or tetra-substituted by methyl, ethyl, n-propyl, isopropyl, n-butyl, sec-butyl, isobutyl or by tert-butyl, or phenyl and phenoxy radicals substituted by fluorine, chlorine, bromine or iodine.

Alkoxyalkyl is, for example, methoxyethyl, ethoxyethyl, methoxypropyl and ethoxypropyl.

Alkylsulfonyl is, for example, methylsulfonyl, ethylsulfonyl, n-propylsulfonyl, isopropylsulfonyl, tert-butylsulfonyl, isobutylsulfonyl and n-butylsulfonyl.

Alkylene is, for example, $-CH_2CH_2-$, $-CH_2CH_2CH_2-$, $-(CH_2)_4-$ and $-(CH_2)_5-$.

Alkoxycarbonyl is, for example, methoxycarbonyl, ethoxycarbonyl, n-propoxycarbonyl and isopropoxycarbonyl.

Alkylsulfinyl is, for example, methylsulfinyl, ethylsulfinyl, n-propylsulfinyl and isopropylsulfinyl.

Alkenyloxy is to be understood as being, straight-chained or branched alkenyloxy, for example vinyloxy, allyloxy, methallyloxy, 1-methylvinyloxy or but-2-en-1-yloxy.

Haloalkenyloxy is, for example, 3,3-difluorobut-2-en-1-yloxy.

Alkynyloxy is to be understood as being, straight-chained or branched alkynyloxy, for example ethynyloxy and but-2-yn-1-yloxy.

Alkoxycarbonylalkoxy is, for example, methoxycarbonylethoxy and ethoxycarbonylethoxy.

Alkoxycarbonylalkenyloxy is, for example, 4-methoxycarbonyl-but-2-en-1-yloxy.

Alkoxyalkoxycarbonylalkyl is, for example, 2-ethoxyethoxycarbonyleth-1-yl.

Cycloalkoxycarbonylalkoxy is, for example, cyclohexyloxycarbonylethoxy.

Cycloalkylmethoxy is, for example, cyclopentylmethoxy and cyclohexylmethoxy.

Alkenyloxyalkyl is to be understood as being straight-chained or branched alkenyloxyalkyl, for example vinyloxyethyl, allyloxymethyl, methallyloxyethyl, 1-methylvinyloxyethyl or but-2-en-1-yloxyethyl.

Alkynyloxyalkyl is to be understood as being, straight-chained or branched alkynyloxyalkyl, for example ethynyloxyethyl or but-2-yn-1-yloxymethyl.

Alkylthiocarbonylalkoxy is, for example, ethylthiocarbonylethoxy.

Alkynyloxycarbonylalkoxy is to be understood as being, for example, straight-chained or branched alkynyloxycarbonylalkoxy, for example ethynyloxycarbonylethoxy and but-2-yn-1-yloxycarbonylethoxy.

Benzyloxycarbonylalkoxy is, for example, benzyloxycarbonylmethoxy and benzyloxycarbonylethoxy.

Alkylbenzyloxy is, for example, 4-methylbenzyloxy, 2-ethylbenzyloxy and 4-isopropylbenzyloxy.

Cyanoalkyl is, for example, 2-cyanoethyl, 3-cyano-n-propyl and 3-cyano-n-butyl.

Alkylcarbamoyloxy is, for example, methylcarbamoyloxy and ethylcarbamoyloxy.

The above-mentioned compounds of formulae I and 11 are known or can be prepared analogously to known methods. These compounds are described especially in the patent publications mentioned in the introduction to the description.

The compounds of formula I that correspond to the formula

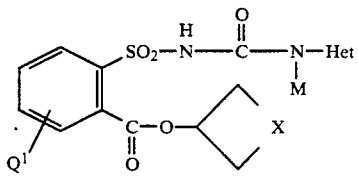

can be prepared, for example, by a) reacting a phenylsulfonamide of the formula

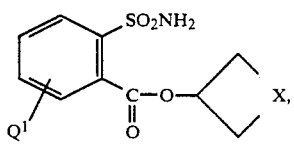

wherein $Q^1$ and X are as defined under formula 1, in the presence of a base with an N-pyrimidinyl or N-triazinyl carbamate of the formula

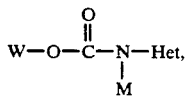

wherein W is unsubstituted or substituted phenyl and M and Het are as defined under formula I, or b) reacting a sulfonyl carbamate of the formula

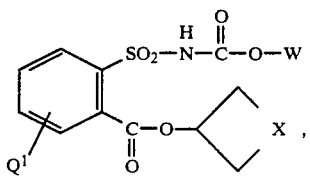

wherein W, X and $Q^1$ are as defined above, in the presence of a base with an amine of the formula

wherein Het is as defined under formula I, or c) reacting a phenylsulfonamide of the formula

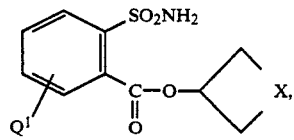

wherein $Q^1$ and X are as defined above, in the presence of a base with an N-pyrimidinyl or N-triazinyl isocyanate of the formula

wherein Het is as defined under formula I.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylfonnamide, diethylformamide or N-methylpyrrolidone. The reaction temperatures are preferably from -20° to +120° C.

The reactions generally proceed in a slightly exothennic manner and can be carried out at room temperature. In order to reduce the reaction time or also to initiate the reaction, it is expedient to heat the reaction mixture at boiling point for a short time. The reaction times can also be shortened by adding a few drops of a base as reaction catalyst. Suitable bases are especially tertiary amines, such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. It is, however, also possible to use inorganic bases, such as hydrides, such as sodium or calcium hydride, hydroxides, such as sodium and potassium hydroxide, carbonates, such as sodium and potassium carbonate, or hydrogen carbonates, such as potassium and sodium hydrogen carbonate.

The end products of formula I can be isolated by concentrating and/or evaporating the solvent and can be purified by recrystallising or triturating the solid residue in solvents in which they are not readily soluble, such as ethers, aromatic hydrocarbons or chlorinated hydrocarbons.

The phenylsulfonamides can be prepared from the corresponding phenyl sulfochlorides of the formula

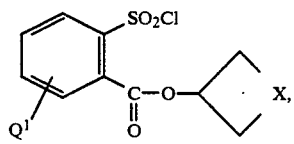

wherein $Q^1$ and X are as defined above, by reaction with ammonia. Such reactions are known and are familiar to the person skilled in the art.

The phenyl sulfochlorides are prepared by reacting the correspondingly substituted 2-chlorosulfonylbenzoyl chlorides (see, for example, D. Davis, Soc. 2042, 2044 (1932)) in the presence of a base with a compound of the formula

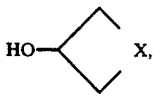

wherein X is as defined above. Such reactions are known and are familiar to the person skilled in the art.

The phenyl sulfochlorides in which X is oxygen can also be prepared by reacting 2-isopropylthiobenzoic acid (see, for example, H. Gilman, F. J. Webb, J. Am. Chem. Soc. 71, 4062–4063) with thionyl chloride to form the corresponding benzoic acid chloride which is then converted using 3-hydroxy-oxetane in the presence of a base into the corresponding 2-isopropylthiobenzoic acid oxetan-3-yl ester in order finally to obtain the sulfochloride by reaction with chlorine. Such reactions are known and are familiar to the person skilled in the art.

3-hydroxyoxetane and 3-hydroxythietane and the preparation thereof are known (see, for example, B. Lamm et al., Acta Chem. Scand. 28, 701 (1974) or J. Org. Chem. 48, 2953–2956 (1983)).

The sulfonyl carbamates can be obtained, for example, by reacting the sulfonamides with diphenyl carbamate in the presence of a base. Such reactions are known and are familiar to the person skilled in the art.

The amines of the formula H2N-Het are described in European Patent Applications Nos. 0 007 687, 0 030 138, 0 073 562 and 0 126 711 and in U.S. Pat. No. 4,579,584.

Processes for the preparation of N-pyrimidinyl and N-triazinyl carbamates are described, for example, in EP-A-0 10 1 670.

The preparation of N-[2-(oxetan-3-yloxycarbonyl)-phenylsulfonyl]-N'-(4-methoxy-6-methyl-1,3,5-triazinyl)-urea will be described by way of example:

A mixture of 15.7 g of 2-isopropylthiobenzoic acid and 15.7 g of thionyl chloride is heated very slowly to reflux and maintained under reflux until the evolution of gas has ceased. By evaporating off all the excess thionyl chloride, 17.3 g of unpurified 2-isopropylthiobenzoic acid chloride are obtained in the form of a yellow oil.

A mixture of 12.9 g of 2-isopropylthiobenzoic acid chloride and 20 ml of absolute toluene is added dropwise at a temperature of from 15° to 20° C. to a mixture of 4.44 g of 3-hydroxy-oxetane, 6.64 g of pyridine and 60 ml of absolute toluene. The resulting suspension is stirred for 2 hours at a temperature of from 20° to 25° C. and for a further 3 hours at a temperature of from 40° to 45° C. Water is added to the reaction mixture and the organic phase is washed with water, dried and concentrated by evaporation to yield 12.6 g of 2-isopropylthiobenzoic acid oxetan-3-yl ester in the form of a pale yellow oil.

1 1.2 g of chlorine are introduced at a temperature of from −5° to 0° C. over a period of 1 hour into a mixture of 12.6 g of 2-isopropylthiobenzoic acid oxetan-3-yl ester, 12.9 g of sodium acetate and 100 ml of 50 % acetic acid and then the batch is stiffed at a temperature of 0° C. for 15 minutes. Methylene chloride is added to the reaction mixture and the organic phase is washed with ice-water and dried to yield a methylene chloride solution of 2-(oxetan-3-yloxycarbonyl)-phenyl sulfochloride which is used without further purification.

2.5 g of ammonia are introduced over a period of 45 minutes at a temperature of from 0° to 5° C. into a methylene chloride solution of 2-(oxetan-3-yloxycarbonyl)-phenyl sulfochloride. Water is added to the reaction mixture and the organic phase is washed with water, dried, concentrated by evaporation and crystallised from a methylene chloride/diethyl ether mixture to yield 6.7 g of 2-(oxetan-3-oxycarbonyl)-phenylsulfonamide having a melting point of from 169° to 170° C.

A mixture of 1.52 g of diazabicyclo[5.4.0]undec-7-ene(1.5-5) and 5 ml of absolute dioxane is added dropwise at from 20° to 25° C. to a mixture of 2.57 g of 2-(oxetan-3-yloxycarbonyl)-phenylsulfonamide, 2.6 g of 4-methoxy-6-methyl-1,3,5-triazinylphenyl carbamate and 40 ml of absolute dioxane and then the batch is stirred for 4 hours at a temperature of from 20° to 25° C. It is then introduced into water, and 10 % hydrochloric acid is added dropwise until a pH of 5 has been established. The batch is extracted with ethyl acetate and the organic phase is dried, concentrated by evaporation and crystallised from ethyl acetate to yield 2.8 g of N-[2-(oxetan-3-yloxycarbonyl)phenylsulfonyl]-N'-(4-methoxy-6-methyl-1,3,5-triazinyl)-urea having a melting point of from 162° to 163° C. (decomposition).

The compounds of formula II, especially those of the formula

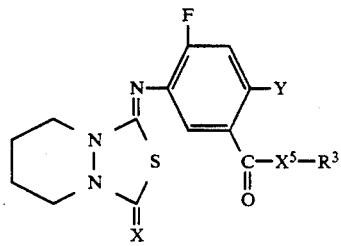

are prepared, for example, by converting an isothiocyanatobenzoic acid ester of the formula

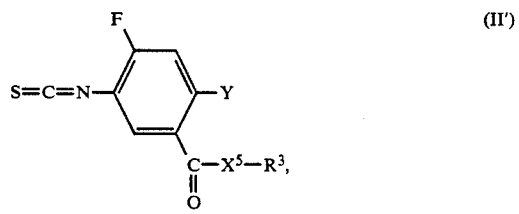

(II')

wherein X, Y, X⁵ and R³ are as defined under formula II, using a hexahydropyridazine, into the compound of the formula

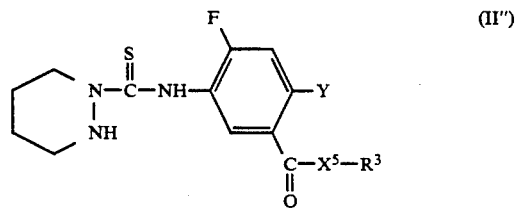

(II″)

and then reacting the latter with a compound of the formula

CY'Cl₂ (II‴), wherein Y' is oxygen or sulfur, in the presence of a base.

The isothiocyanatobenzoic acid esters can be prepared by reacting an aniline of the formula

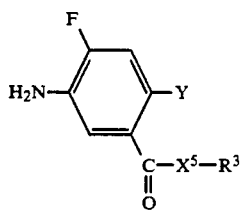

wherein Y, $X^5$ and $R^3$ are as defined above, with thiophosgene.

The reaction of the benzoic acid esters of formula II' with hexahydropyridazine is advantageously carried out in a solvent that is inert under the reaction conditions and at temperatures of from −5° C. up to the boiling temperature of the solvent, especially at from 0° to +50° C., room temperature being especially preferred. Suitable solvents for this reaction are, for example, toluene, xylene, ethyl acetate or acetonitrile.

The reaction of the compound of formula II'' with the compound of formula II''' is advantageously carried out in a solvent that is inert under the reaction conditions and at low temperatures, preferably at from 0° to +50° C., especially preferably at from 0° to +15° C. Suitable bases for this reaction are, for example, pyridine, triethylamine or N,N-dimethylaniline.

Suitable solvents are, for example, 1,2-dichloroethane, dichloromethane or toluene.

The preparation of 9-[4-chloro-2-fluoro-5-(methoxycarbonylmethylthiocarbonyl)-phenylimino]-8-thia-1,6-diazabicyclo[4.3.0]nonan-7-one is given by way of example:

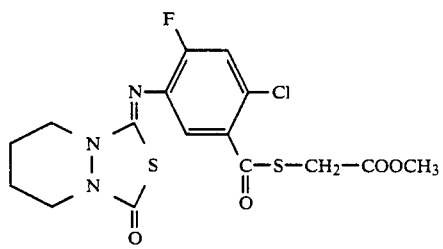

48 g of 2-chloro-4-fluoro-5-nitrobenzoic acid chloride are added dropwise, with stirring, at room temperature to a solution of 20 ml of thioglycolic acid methyl ester in 100 ml of ethyl acetate. The batch is stirred for 18 hours and then the solvent is evaporated off in vacuo to yield 19 g of 2-chloro-4-fluoro-5-nitrothiobenzoic acid (methoxycarbonylmethyl) ester in the form of an oil having $n_D^{23}$: 1.5709.

10.4 g of the resulting 2-chloro-4-fluoro-5-nitrothiobenzoic acid (methoxycarbonylmethyl) ester are hydrogenated with hydrogen under normal pressure in 150 ml of tetrahydrofuran at a temperature of from 20° to 25° C. in the presence of 2 g of Raney nickel catalyst. When the stoichiometric amount of hydrogen has been consumed, the catalyst is separated off and the solution is concentrated by evaporation to yield 8.6 g of 5-amino-2-chloro-4-fluorothiobenzoic acid (methoxycarbonylmethyl) ester having a melting point of from +88° to +89° C.

A solution of 3.8 g of the resulting 5-amino-2-chloro-4-fluorothiobenzoic acid (methoxycarbonylmethyl) ester in 100 ml of dichloromethane is added dropwise at from 25° to 30° C. to a suspension of 6 g of calcium carbonate, 4 ml of thiophosgene, 20 ml of dichloromethane and 20 ml of water. When the evolution of carbon dioxide has ceased, the batch is stirred for a further 18 hours at room temperature. After filtering and washing with water, the organic phase is separated off, dried over sodium sulfate and then concentrated by evaporation to yield 4.8 g of 2-chloro-4-fluoro-5-isothiocyanatothiobenzoic acid (methoxycarbonylmethyl) ester in the form of an oil which is used without further purification in the next reaction step.

A solution of 4.8 g of the resulting 2-chloro-4-fluoro-5-isothiocyanatothiobenzoic acid (methoxycarbonylmethyl) ester in 50 ml of toluene is added dropwise, with stirring, at from 20° to 250° C. to a solution of 1.4 g of hexahydropyridazine in 20 ml of toluene. The batch is then stirred for a further 8 hours at room temperature and is then concentrated by evaporation in vacuo to yield 4.4 g of 2-chloro-4-fluoro-5-(1-hexahydropyridazinylthiocarbonylamino)-thiobenzoic acid (methoxycarbonylmethyl) ester in resinous form.

8 ml of a 20 % solution of phosgene in toluene are added dropwise, with stirring, at a temperature of 0° C. to a solution of 4.4 g of the resulting 2-chloro-4-fluoro-5-(1-hexahydropyridazinylthiocarbonylamino)-thiobenzoic acid (methoxycarbonylmethyl) ester and 5 ml of pyridine in 10 ml of dichloromethane. The reaction mixture is then stirred for a further 2 hours and then poured into ice-water. The organic phase is separated off and dried over sodium sulfate. After concentration by evaporation and subsequent chromatogaphic purification of the resulting oily product, 3 g of 9-[4-chloro-2-fluoro-5 -(methoxycarbonylmethylthiocarbonyl)-phenylimino]-8-thia- 1,6-diazabicyclo[4.3.0]nonan-7-one having $n_D^{19}$ 1.5727 are obtained.

Preferred are the sulfonylureas of formula I $$Z-SO_2-NH-CO-\overset{M}{\underset{|}{N}}-Het, \tag{I}$$

wherein

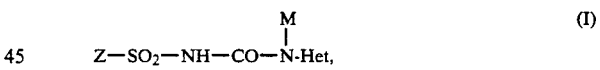

Z is a radical

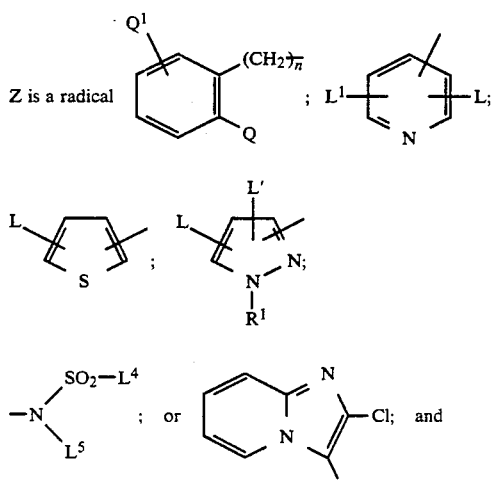

Het is the radical 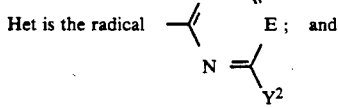

M is hydrogen; or $C_1$-$C_4$alkyl;

Q is halogen; nitro; $C_1$-$C_6$alkyl; $C_1$-$C_6$haloalkyl; $C_2$-$C_6$alkenyl; $C_2$-$C_6$haloalkenyl; $C_2$-$C_6$alkynyl; $C_3$-$C_6$haloalkynyl; —$SO_2N(CH_3)_2$; —$COOR_2$; —COOR'; or —(A)—$R_2$;

$R^1$ is hydrogen; or $C_1$-$C_4$alkyl;

$R^2$ is $C_1$-$C_5$alkyl; $C_2$-$C_5$alkenyl; $C_2$-$C_5$alkynyl; $C_1$-$C_5$haloalkyl; $C_1$-$C_4$alkoxy-$C_1$-$C_4$alkyl; $C_2$-$C_5$haloalkenyl; or $C_2$-$C_5$haloalkynyl;

R' is oxetan-3-yl; or thietan-3-yl;

A is oxygen; sulfur, -SO2-; or -O-SO2-;

$Q^1$ is hydrogen; nitro; halogen; $OCH_3$; $OCHF_2$; $CH_3$; or $SCH_3$;

L is halogen; nitro; $C_1$-$C_5$alkyl; —A—$R_2$; —$COOR^2$, —CO—$NH_2$; —CO—$NHC_1$-$C_4$alkyl; or —CO—$N(C_1$-$C_4$alkyl$)_2$;

L' is hydrogen; or chlorine;

$L^1$ is hydrogen; nitro; $C_1$-$C_4$alkyl; halogen; $C_1$-$C_4$alkoxy; $C_1$-$C_4$haloalkyl; or $C_1$-$C_4$haloalkoxy;

$L^4$ is $C_1$-$C_6$alkyl;

$L^5$ is $C_1$-$C_6$alkyl; or $L^4$ and $L^5$ together are a $C_3$-$C_4$alkylene badge;

$X^2$ is $C_1$-$C_4$haloalkoxy; $C_1$-$C_4$haloalkyl; $C_1$-$C_4$alkoxy; $C_1$-$C_4$alkyl; halogen; $SCH_3$; cyclopropyl; dimethylamino; methylamino; or $C_1$-$C_4$alkoxy-$C_1$-$C_4$alkyl;

$Y^2$ is $C_1$-$C_4$haloalkoxy; $C_1$-$C_4$haloalkyl; $C_1$-$C_4$alkoxy; $C_1$-$C_4$alkyl; cyclopropyl; dimethylamino; methylamino; or $C_1$-$C_4$alkoxy-$C_1$-$C_4$alkyl; and E is CH; or N; and the agrochemically acceptable salts thereof.

Also preferred are the sulfonylureas of formulae Ia, Ib, Ic, Id, Ie, If and Ig:

Sulfonylureas of formula Ia,

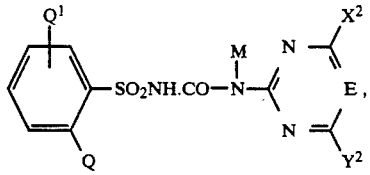

(Ia)

wherein

M is hydrogen; or $C_1$-$C_4$alkyl;

Q is halogen; nitro; $C_1$-$C_6$haloalkyl; $C_2$-$C_6$alkenyl; $C_2$-$C_6$haloalkenyl; $C_2$-$C_6$alkynyl; —$SO_2N(CH_3)_2$; —$COOR_2$; —COOR'; or —(A)—$R^2$;

A is oxygen; sulfur, or —$SO_2$—;

$R^2$ is $C_1$-$C_5$alkyl; $C_3$-$C_6$alkenyl; $C_3$-$C_6$alkynyl; $C_1$-$C_5$haloalkyl; $C_1$-$C_4$alkoxy-$C_1$-$C_4$alkyl; $C_2$-$C_5$haloalkenyl; or $C_2$-$C_5$haloalkynyl;

R' is oxetan-3-yl; or thietan-3-yl;

$Q^1$ is hydrogen; nitro; halogen; $OCH_3$; $OCHF_2$; $CH_3$; or $SCH_3$;

$X^2$ is $C_1$-$C_4$haloalkoxy; $C_1$-$C_4$haloalkyl; $C_1$-$C_4$alkoxy; $C_1$-$C_4$alkyl; halogen; $SCH_3$; cyclopropyl; dimethylamino; methylamino; or $C_1$-$C_4$alkoxy-$C_1$-$C_4$alkyl;

$Y_2$ is $C_1$-$C_4$haloalkoxy; $C_1$-$C_4$haloalkyl; $C_1$-$C_4$alkoxy; $C_1$-$C_4$alkyl; cyclopropyl; dimethylamino; methylamino; or $C_1$-$C_4$alkoxy-$C_1$-$C_4$alkyl; and E is CH; or N;

and the agochemically acceptable salts thereof.

Especially preferred are the sulfonylureas of formula Ia, wherein

M is hydrogen; or methyl;

Q is $C_1$-$C_6$haloalkyl, especially $C_1$-$C_6$fluoroalkyl; $C_2$-$C_6$haloalkenyl, especially $C_2$-$C_6$fluoroalkenyl; —(A)—$R_2$; —COOR'; or —$COOR_2$;

A is oxygen; or sulfur;

$R^2$ is $C_1$-$C_6$haloalkyl, especially $C_1$-$C_6$fluoroalkyl or $C_1$-$C_6$Chloroalkyl; $C_1$-$C_2$alkoxy-$C_1$-$C_3$alkyl; or $C_1$-$C_2$alkyl;

R' is oxetan-3-yl; or thietan-3-yl;

E is N; or CH;

$Q^1$ is hydrogen; and $X^2$ and $Y^2$, each independently of the other, is $C_1$-$C_4$alkyl, especially methyl; $C_1$-$C_4$-alkoxy, especially methoxy; $C_1$-$C_4$haloalkoxy, especially $C_1$-$C_2$-fluoroalkoxy; or halogen, especially chlorine.

Sulfonylureas of formula Ib,

Sulfonylureas of formula Ib,

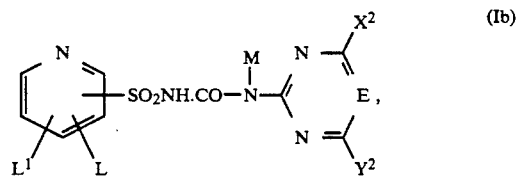

(Ib)

wherein 'M is hydrogen; or $C_1$-$C_4$alkyl;

L is halogen; nitro; $C_1$-$C_5$alkyl; —A—$R_2$; —$COOR_2$; —NH($C_1$-$C_4$alkyl); or —N($C_1$-$C_4$alkyl$)_2$; —CO—$NH_2$; —CO—$NHC_1$-$C_4$alkyl; or —CO—N($C_1$-$C_4$alkyl$)_2$;

$L^1$ is hydrogen; nitro; $C_1$-$C_4$alkyl; halogen; $C_1$-$C_4$alkoxy; $C_1$-$C_4$haloalkyl; or $C_1$-$C_4$haloalkoxy;

$X^2$ is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl;

$Y^2$ is $C_1$-$C_4$haloalkoxy; $C_1$-$C_4$haloalkyl; $C_1$-$C_4$alkoxy; $C_1$-$C_4$ alkyl; dimethylamino; methylamino; or $C_1$-$C_4$alkoxy-$C_1$-$C_4$alkyl;

A is oxygen; sulfur; or —$SO_2$—;

$R^2$ is $C_1$-$C_5$alkyl; $C_3$-$C_6$alkenyl; $C_3$-$C_6$alkynyl; $C_1$-$C_5$haloalkyl; $C_1$-$C_4$alkoxy-$C_1$-$C_4$alkyl; $C_2$-$C_5$haloalkenyl; or $C_2$-$C_5$haloalkynyl;

E is CH; or N;

and the agrochemically acceptable salts thereof.

The invention also relates especially to the compounds of formula Ib' or Ib"

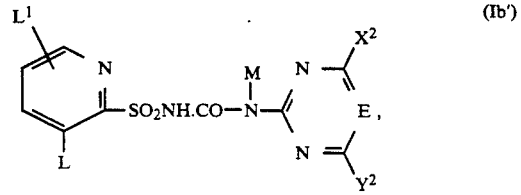

(Ib')

or

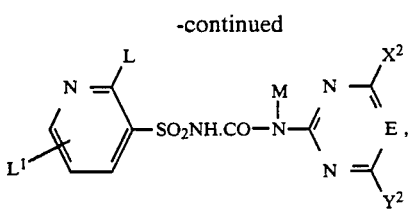

wherein the substituents L, L¹, M, X², Y² and E are as defined above.

Sulfonylureas of formula Ic,

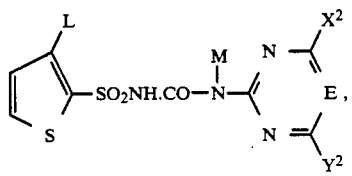

wherein
L is halogen; nitro; $C_1$-$C_5$alkyl; $C_1$-$C_5$alkylsulfonyl; —COOR$_2$; —CO—NH$_2$; —CO—NHC$_1$-C$_4$alkyl; or —CO—N(C$_1$-C$_4$alkyl)$_2$;
R² is $C_1$-$C_5$alkyl; $C_1$-$C_5$haloalkyl; $C_2$-$C_6$alkenyl; $C_2$-$C_6$haloalkenyl; $C_2$-$C_6$alkynyl; $C_3$-$C_6$haloalkynyl; or $C_1$-$C_4$alkoxy-$C_1$-$C_4$alkyl;
X² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl;
Y² is $C_1$-$C_4$haloalkoxy; $C_1$-$C_4$haloalkyl; $C_1$-$C_4$alkoxy; $C_1$-$C_4$alkyl; cyclopropyl; dimethylamino; methylamino; or $C_1$-$C_4$alkoxy-$C_1$-$C_4$alkyl; and
E is CH; or N; and the agrochemically acceptable salts thereof.

Sulfonylureas of formula Id

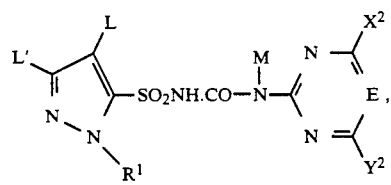

wherein
M is hydrogen; or $C_1$-$C_4$alkyl;
L is $C_1$-$C_5$alkyl; $C_1$-$C_5$alkylsulfonyl; —COOR$_2$; —CO—NH$_2$; —CO—NHC$_1$-C$_4$alkyl; or —CO—N(C$_1$-C$_4$alkyl)$_2$;
L' is hydrogen; or chlorine;
R¹ is hydrogen; $C_1$-$C_4$alkyl; or pyridyl;
R² is $C_1$-$C_5$alkyl; $C_1$-$C_5$haloalkyl; $C_1$-$C_4$alkoxy-$C_1$-$C_4$alkyl; $C_3$-$C_6$haloalkenyl; or $C_3$-$C_6$-haloalkynyl;
X² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl;
Y² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy $C_1$-$C_4$alkyl; and E is CH; or N;
and the agrochemically acceptable salts thereof.

Sulfonylureas of formula Ie

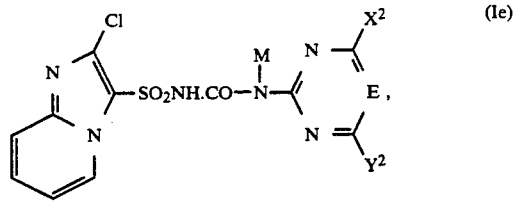

wherein
X² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl;
Y² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl; and
E is CH; or N;
and the agrochemically acceptable salts thereof.

Sulfonylureas of formula If

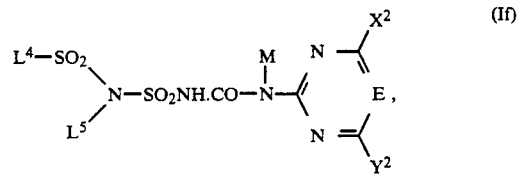

wherein
L⁴ is $C_1$-$C_6$alkyl;
L⁵ is $C_1$-$C_6$alkyl; or
L⁴ and L⁵ together are a $C_2$-$C_6$alkylene bride;
X² is $C_1$-$C_4$haloalkoxy; $C_1$-$C_4$haloalkyl; $C_1$-$C_4$alkoxy; $C_1$-$C_4$alkyl; dimethylamino; methylamino; or $C_1$-$C_4$alkoxy-$C_1$-$C_4$alkyl;
Y² is $C_1$-$C_4$haloalkoxy; $C_1$-$C_4$haloalkyl; $C_1$-$C_4$alkoxy; $C_1$-$C_4$ alkyl; dimethylamino; methylamino; or $C_1$-$C_4$alkoxy-$C_1$-$C_4$alkyl; and
E is CH; or N;
and the agrochemically acceptable salts thereof.

Sulfonylureas of formula Ig

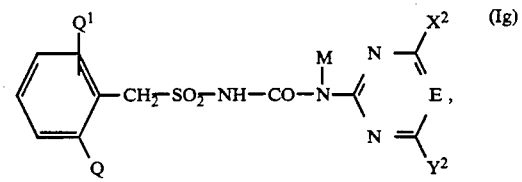

wherein Q¹, Q, M, E, X² and Y² are as defined under formula Ia. Especially preferred is the compound of formula Ig wherein Q¹ is hydrogen, Q is COOCH$_3$, M is hydrogen, E is CH and each of X² and Y² is methoxy. (Compound No. 0.001).

The compounds of Tables 1 to 8 may be mentioned as especially preferred individual compounds:

TABLE 1

As compounds of formula Ia

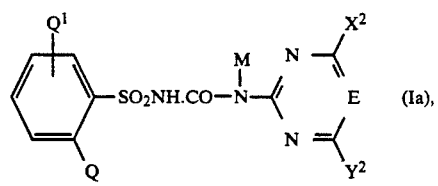

(Ia),

| Comp. No. | $Q^1$ | M | E | Q | $X^2$ | $Y^2$ |
|---|---|---|---|---|---|---|
| 1.001 | H | H | N | $OCH_2CH_2Cl$ | $CH_3$ | $OCH_3$ |
| 1.002 | H | H | N | $SCH_2CH_2F$ | $CH_3$ | $OCH_3$ |
| 1.003 | H | H | N | $CH_2CH_2CF_3$ | $CH_3$ | $OCH_3$ |
| 1.004 | H | H | N | $CH=CHCF_2CH_3$ | $CH_3$ | $OCH_3$ |
| 1.005 | H | H | N | $CH_2CH_2CF_2CH_3$ | $CH_3$ | $OCH_3$ |
| 1.006 | H | H | N | $SCH_2CH_2F$ | $CH_3$ | $OCH_3$ |
| 1.007 | H | H | N | $SCH_2CHF_2$ | $CH_3$ | $OCH_3$ |
| 1.008 | H | H | N | $SCH_2CH_2ClF$ | $CH_3$ | $OCH_3$ |
| 1.009 | H | H | N | $OCH_2CH_2-F$ | $CH_3$ | $OCH_3$ |
| 1.010 | H | H | N | $COOCH_3$ | $O-C_2H_5$ | cyclo-$C_3H_5$ |
| 1.011 | H | H | N | $COOCH_3$ | $O-C_2H_5$ | $NHCH_3$ |
| 1.012 | H | $CH_3$ | N | $COOCH_3$ | $OCH_3$ | $CH_3$ |
| 1.013 | H | H | CH | $COOCH_3$ | $CH_3$ | $CH_3$ |
| 1.014 | H | H | CH | $COOC_2H_5$ | $OCH_3$ | Cl |
| 1.015 | H | H | N | $COOCH_3$ | $OCH_3$ | Cl |
| 1.016 | H | H | CH | $NO_2$ | $OCHF_2$ | $CH_3$ |
| 1.017 | H | H | CH | $COOCH_3$ | $OCHF_2$ | $OCHF_2$ |
| 1.018 | H | H | CH | $COOCH_3$ | $OCHF_2$ | $CH_3$ |
| 1.019 | H | H | N | $OCH_2C≡CH$ | $OC_2H_5$ | $CH_3$ |
| 1.020 | H | H | N | $OCH_2CH_2OCH_3$ | $OCH_3$ | $CH_3$ |
| 1.021 | H | H | N | $OCF_2CF_3$ | $OCH_3$ | $OCH_3$ |
| 1.022 | H | H | N | $OCH_2CHF_2$ | $OCH_3$ | $CH_3$ |
| 1.023 | H | H | N | $OCH_2CHFCl$ | $OCH_3$ | $CH_3$ |
| 1.024 | H | H | N | $SCH_2CH_2Cl$ | $OCH_3$ | $CH_3$ |
| 1.025 | H | H | CH | $COOCH_3$ | $CH_3$ | cyclo-$C_3H_5$ |
| 1.026 | H | H | N | $-CH=CHCF_3$ | $OCH_3$ | $CH_3$ |
| 1.027 | H | H | CH | $COOCH_3$ | $OCH_3$ | $OCHF_2$ |
| 1.028 | H | H | N | $COOCH_3$ | $OCH_3$ | cyclo-$C_3H_5$ |
| 1.029 | H | H | N | $OCH_2CH=CH_2$ | $OC_2H_5$ | $CH_3$ |
| 1.030 | H | H | N | $OCH_2C≡CH$ | $OCH_3$ | $CH_3$ |
| 1.031 | H | H | N | $OCH_2CH=CH_2$ | $OCH_3$ | $CH_3$ |
| 1.032 | H | H | N | $OCHF_2$ | $OCH_3$ | $C_2H_5$ |
| 1.033 | H | H | N | $OCHF_2$ | $OCH_3$ | $N(CH_3)_2$ |
| 1.034 | H | H | N | Cl | $OCH_3$ | $CH_3$ |
| 1.035 | H | H | N | $SO_2C_2H_5$ | $OCH_3$ | $CH_3$ |
| 1.036 | H | H | N | $SO_2$-(n)-$C_3H_7$ | $OCH_3$ | $CH_3$ |
| 1.037 | 6-$CH_3$ | H | N | $COOCH_3$ | $NHCH_3$ | $OCH_2CF_3$ |
| 1.038 | 6-$CH_3$ | H | N | $COOC_2H_5$ | $N(CH_3)_2$ | $OCH_2CF_3$ |
| 1.039 | H | H | N | $COOCH_3$ | $CH_3$ | $OCH_3$ |
| 1.040 | H | H | N | $OCH_2CH_2OCH_3$ | $OCH_3$ | $OCH_3$ |
| 1.041 | H | H | N | COO-(oxetanyl) | $CH_3$ | $OCH_3$ |
| 1.042 | H | H | CH | COO-(oxetanyl) | $CH_3$ | $CH_3$ |
| 1.043 | H | H | CH | COO-(oxetanyl) | $CH_3$ | $OCH_3$ |
| 1.044 | H | H | CH | COO-(oxetanyl) | $OCH_3$ | $OCH_3$ |
| 1.045 | H | H | CH | COO-(oxetanyl) | Cl | $OCH_3$ |

TABLE 1-continued

As compounds of formula Ia

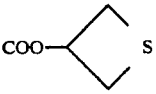

(Ia),

| Comp. No. | $Q^1$ | M | E | Q | $X^2$ | $Y^2$ |
|---|---|---|---|---|---|---|
| 1.046 | H | H | CH | COO—(thietane) | $OCH_3$ | $OCH_3$ |
| 1.047 | H | H | CH | COO—(thietane) | Cl | $OCH_3$ |
| 1.048 | H | H | N | COO—(thietane) | $CH_3$ | $OCH_3$ |
| 1.049 | H | H | N | COO—(oxetane) | $CH_3$ | $OCH_3$ |
| 1.050 | H | H | N | COO—(oxetane) | $OCH_3$ | $OCH_3$ |

TABLE 2

As compounds of formula Ib

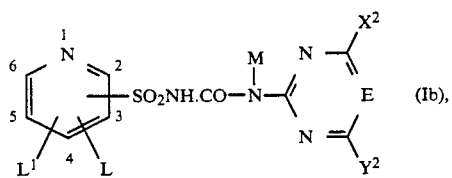

(Ib),

| Comp. No. | M | E | L | $L^1$ | $X^2$ | $Y^2$ | Pos. pyridine[1] |
|---|---|---|---|---|---|---|---|
| 2.001 | H | CH | 3-CON(CH$_3$)$_2$ | H | $OCH_3$ | $OCH_3$ | 2 |
| 2.002 | H | CH | 3-CF$_3$ | H | $OCH_3$ | $OCH_3$ | 2 |
| 2.003 | H | CH | 3-SO$_2$C$_2$H$_5$ | H | $OCH_3$ | $OCH_3$ | 2 |
| 2.004 | H | CH | 3-SO$_2$-(n)-C$_3$H$_7$ | H | $OCH_3$ | $OCH_3$ | 2 |
| 2.005 | H | CH | 3-SO$_2$-(i)-C$_3$H$_7$ | H | $OCH_3$ | $OCH_3$ | 2 |
| 2.006 | H | CH | 2-SO$_2$CH$_2$CH$_2$OCH$_3$ | H | $OCH_3$ | $OCH_3$ | 3 |
| 2.007 | H | CH | 3-SO$_2$CH$_2$CH$_2$OCH$_3$ | H | $OCH_3$ | $OCH_3$ | 2 |
| 2.008 | H | CH | 3-SO$_2$CH$_2$CHCH$_2$ | H | $OCH_3$ | $OCH_3$ | 2 |
| 2.009 | H | N | 2-Cl | H | $OCH_3$ | $CH_3$ | 3 |
| 2.010 | H | CH | 3-Cl | H | $OCH_3$ | $OCH_3$ | 2 |
| 2.011 | H | N | 3-Cl | H | $OCH_3$ | $CH_3$ | 2 |
| 2.012 | H | CH | 3-COOCH$_3$ | 6-CF$_3$CH$_2$O | $OCH_3$ | $OCH_3$ | 2 |

[1] Position of linkage of the sulfonylurea radical to the pyridine system

TABLE 3
As compounds of formula Ic

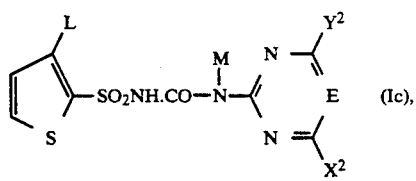

| Comp. No. | M | L | E | $X^2$ | $Y^2$ |
|---|---|---|---|---|---|
| 3.001 | H | COOCH$_3$ | N | CH$_3$ | OCH$_3$ |
| 3.002 | H | COOCH$_3$ | CH | OCH$_2$CF$_3$ | OCH$_3$ |

TABLE 4
As compounds of formula Id

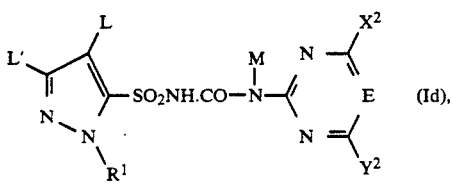

| Comp. No. | M | $R^1$ | L' | L | E | $X^2$ | $Y^2$ |
|---|---|---|---|---|---|---|---|
| 4.001 | H | CH$_3$ | H | COOC$_2$H$_5$ | CH | OCH$_3$ | OCH$_3$ |
| 4.002 | H | pyridin-2-yl | H | COOC$_2$H$_5$ | CH | OCH$_3$ | OCH$_3$ |
| 4.003 | H | CH$_3$ | Cl | COOC$_2$H$_5$ | CH | OCH$_3$ | OCH$_3$ |

TABLE 5
As compounds of formula Ie

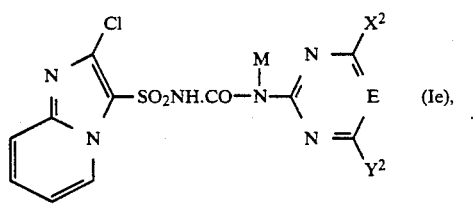

| Comp. No. | M | E | $X^2$ | $Y^2$ |
|---|---|---|---|---|
| 5.001 | H | N | CH$_3$ | O—CH$_3$ |
| 5.002 | H | CH | O—CH$_3$ | O—CH$_3$ |

TABLE 6
As compounds of formula If

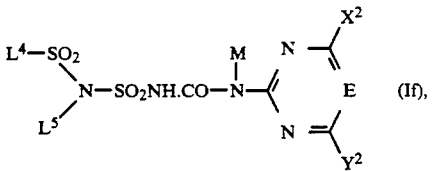

| Comp. No. | M | E | $L^4$ | $L^5$ | $X^2$ | $Y^2$ |
|---|---|---|---|---|---|---|
| 6.001 | H | CH | CH$_3$ | CH$_3$ | O—CH$_3$ | O—CH$_3$ |
| 6.002 | H | N | CH$_3$ | CH$_3$ | O—CH$_3$ | CH$_3$ |
| 6.003 | H | N | CH$_3$ | C$_2$H$_5$ | O—CH$_3$ | O—CH$_3$ |
| 6.004 | H | CH | —(CH$_2$)$_3$— | | O—CH$_3$ | O—CH$_3$ |
| 6.005 | H | N | —(CH$_2$)$_3$— | | O—CH$_3$ | CH$_3$ |
| 6.006 | H | CH | —(CH$_2$)$_4$— | | O—CH$_3$ | O—CH$_3$ |

TABLE 6-continued
As compounds of formula If

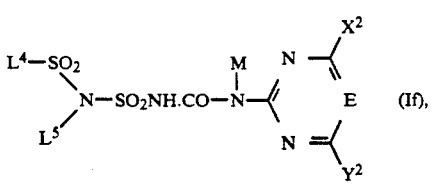

| Comp. No. | M | E | $L^4$ | $L^5$ | $X^2$ | $Y^2$ |
|---|---|---|---|---|---|---|
| 6.007 | H | N | —(CH$_2$)$_4$— | | O—CH$_3$ | CH$_3$ |

Preferred are the compounds of formula II

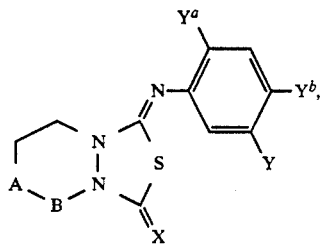

wherein

A—B is —CH$_2$—CH$_2$—; or —CH═CH—;

Y is hydroxy; C$_1$-C$_6$alkyl; C$_1$-C$_6$alkoxy; C$_1$-C$_6$-haloalkoxy; C$_3$-C$_6$alkenyloxy; C$_2$-C$_6$haloalkenyloxy; C$_3$-C$_6$alkynyloxy; phenoxy; C$_5$-C$_6$Cycloalkyloxy; C$_1$-C$_6$alkoxycarbonyl-C$_1$-C$_4$alkoxy; C$_1$-C$_6$alkoxycarbonyl-C$_2$-C$_4$alkenyloxy; C$_1$-C$_6$alkylthiocarbonyl-C$_1$-C$_4$alkoxy; C$_3$-C$_6$alkynyloxycarbonyl-C$_1$-C$_4$alkoxy; benzyloxycarbonyl-C$_1$-C$_4$alkoxy; trifluoromethyl; benzyloxy; chlorobenzyloxy; C$_1$-C$_6$alkylbenzyloxy; C$_2$-C$_6$alkenyl; cyano-C$_1$-C$_6$alkyl; C$_1$-C$_6$alkylcarbamoyloxy; C$_1$-C$_4$alkoxy-C$_1$-C$_4$alkyl; C$_3$-C$_6$alkynyloxy-C$_1$-C$_4$alkyl; C$_3$-C$_6$alkenyloxy-C$_1$-C$_4$alkyl; unsubstituted or halo-substituted C$_5$-C$_6$cycloalkylmethoxy; C$_1$-C$_6$alkoxy-C$_1$-C$_4$-alkoxy; phenethyloxy; C$_5$-C$_6$-cycloalkoxycarbonyl-C$_1$-C$_4$alkoxy; pyrrolidinocarbonyl; unsubstituted or C$_1$-C$_6$alkyl-substituted phenylcarbonyl; —CO—X$_5$—R$^3$;

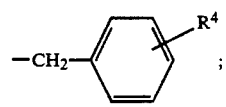

—S(O)$_p$—R$^5$; —O—CH(R$^6$)—CO—OR'; —N═C(CH$_3$)—R$^8$; —NHR$^9$; —S—CH(R$^{10}$)—CO—R$^{11}$; or —O—P(X$^5$)(OC$_2$H$_5$)$_2$;

$Y^a$ and $Y^b$, each independently of the other, is hydrogen; fluorine; chlorine; or bromine; and $R^3$ to $R^{11}$, X, $X^5$ and p are as defined above.

Especially preferred are the compounds of formula II

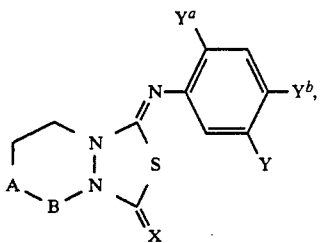 (II)

wherein
A—B is —CH₂—CH₂—; or —CH=CH—;
Y is $C_1$-$C_6$alkoxy; $C_1$-$C_6$haloalkoxy; $C_3$-$C_6$alkenyloxy; $C_2$-$C_6$haloalkenyloxy; $C_3$-$C_6$-alkynyloxy; $C_5$-$C_6$cycloalkyloxy; $C_1$-$C_6$alkoxycarbonyl-$C_1$-$C_4$alkoxy; $C_1$-$C_6$alkoxycarbonyl-$C_2$-$C_4$alkenyloxy; $C_1$-$C_6$alkylthiocarbonyl-$C_1$-$C_4$alkyl; $C_3$-$C_6$alkynyloxycarbonyl-$C_1$-$C_4$alkoxy; cyano-$C_1$-$C_6$alkyl; $C_1$-$C_6$alkylcarbamoyloxy; $C_1$-$C_6$alkoxy-$C_1$-$C_4$alkoxy; phenoxy; benzyloxy; —S(O)$_p$—R⁵; —O—CH(R⁶)—CO—OR⁷; —CO—X⁵—R³; or —S—CH(R¹⁰)—CO—R¹¹;
Yᵃ is hydrogen; fluorine; or chlorine;
Yᵇ is hydrogen; fluorine; chlorine; or bromine;
R³ is hydrogen; $C_1$-$C_6$alkyl; phenyl; $C_5$-$C_6$cycloalkyl; $C_1$-$C_6$alkoxy-$C_1$-$C_4$alkyl; $C_1$-$C_6$alkoxycarbonyl-$C_1$-$C_4$alkyl; or $C_1$-$C_4$alkoxy-$C_1$-$C_4$alkoxycarbonyl-$C_1$-$C_4$alkyl;
R⁵ is $C_1$-$C_6$alkyl; $C_3$-$C_6$alkenyl; or $C_3$-$C_6$alkynyl;
p is 0 or 2;
R⁶ is hydrogen; or $C_1$-$C_6$alkyl;
R⁷ is hydrogen; $C_1$-$C_6$alkyl; $C_1$-$C_6$alkoxy-$C_1$-$C_4$alkyl; tetrahydrofuryl; $C_1$-$C_4$alkoxy-$C_1$-$C_4$alkoxy-$C_1$-$C_4$alkyl; $C_1$-$C_6$alkoxycarbonyl-$C_1$-$C_4$alkyl; or $C_5$-$C_6$Cycloalkyl;
R¹⁰ is hydrogen; or $C_1$-$C_6$alkyl;
R¹¹ is $C_1$-$C_6$alkoxy; $C_5$-$C_6$cycloalkyloxy; 1-pyrrolidinyl; $C_3$-$C_6$alkenyloxy; $C_3$-$C_6$alkynyloxy; $C_1$-$C_6$alkylthio; $C_1$-$C_6$haloalkoxy; $C_1$-$C_4$alkoxycarbonyl-$C_1$-$C_4$alkoxy; α,α-dimethylbenzylamino; —OC₂H₄S(O)₂—($C_1$-$C_6$alkyl); —OC₂H₄S—($C_1$-$C_6$alkyl); —OC₂H₄S(O)₂-(phenyl); —OC₂H₄S-(phenyl);

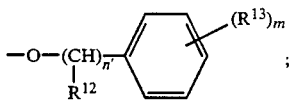

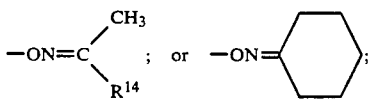

m is 0; 1; 2; or 3;
n' is 0; or 1;
R¹² is halogen; or $C_1$-$C_4$alkyl;
R¹³ is phenyl; benzyl; or methoxy-$C_1$-$C_4$alkyl;
R¹⁴ is Styryl; cyano-$C_1$-$C_4$alkyl; tetrahydrofuran-2-yl, thienyl or pyridin-2-yl;
X is oxygen; or sulfur; and
X⁵ is oxygen; or sulfur.

Special prominence is to be given to the compounds of formulae IIa to IId:

Compounds of formula IIa

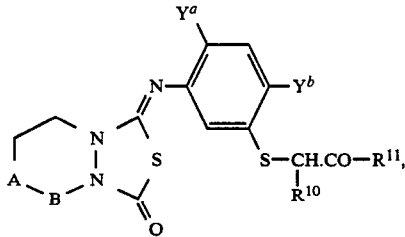 (IIa)

wherein
A-B, Yᵃ, Yᵇ, R¹⁰ and R¹¹ are as defined above.

Compounds of formula IIb

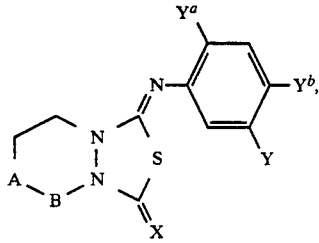 (IIb)

wherein
y is $C_1$-$C_6$alkoxy; $C_3$-$C_6$alkenyloxy; $C_3$-$C_6$alkynyloxy; $C_1$-$C_6$alkoxycarbonyl-$C_1$-$C_4$-alkoxy; $C_1$-$C_6$alkylthiocarbonyl-$C_1$-$C_4$alkoxy; $C_3$-$C_6$alkynyloxycarbonyl-$C_1$-$C_4$alkoxy; $C_1$-$C_6$alkylthio; $C_1$-$C_6$alkylsulfonyl; $C_3$-$C_6$alkynylthio; $C_3$-$C_6$alkenylthio; $C_5$-$C_6$cycloalkoxy; phenoxy; benzyloxy; cyano-$C_1$-$C_6$alkyl; $C_1$-$C_6$alkoxy-$C_1$-$C_4$-alkoxy; and
A-B, Yᵃ and Yᵇ are as defined above.

Compounds of formula IIc

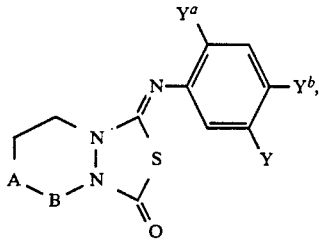 (IIc)

wherein
Y is —CO—X⁵—R³;
R³ is hydrogen; $C_1$-$C_6$alkyl; phenyl; $C_5$-$C_6$cycloalkyl; $C_1$-$C_6$alkoxy-$C_1$-$C_4$alkyl; $C_3$-$C_6$-alkynyl; $C_3$-$C_6$alkenyl; benzyl; $C_1$-$C_6$alkoxycarbonyl-$C_1$-$C_4$alkyl; or $C_1$-$C_4$alkoxy-$C_1$-$C_4$alkoxycarbonyl-$C_1$-$C_4$alkyl; and
X⁵ is oxygen; or sulfur; and
A-B, Yᵃ and Yᵇ are as defined above.

Compounds of formula IId

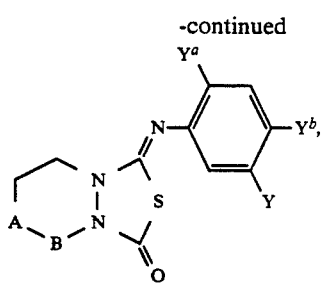
(IId)

wherein
Y is —O—CH(R⁶)—CO—OR⁷;
R⁶ is hydrogen; or C₁-C₆alkyl;
R⁷ is hydrogen; C₁-C₆alkyl; C₃-C₆alkynyl; C₃-C₆alkenyl; C₁-C₆alkoxy-C₁-C₄alkyl; tetrahydrofuryl; C₁-C₄alkoxy-C₁-C₄alkoxy-C₁-C₄alkyl; C₁-C₆alkoxycarbonyl-C₁-C₄-alkyl; or C₅-C₆cycloalkyl; and
A-B, Y$^a$ and Y$^b$ are as defined above.

The invention relates especially to the compounds of formula II and of formulae IIa to IId wherein
A-B is —CH₂—CH₂—; and
Y, Y$^a$, Y$^b$ and the radicals R¹⁰ and R¹¹ are as defined above.

The invention relates also to the compounds of formula 11 and of formulae IIa to IId wherein
A—B is —CH=CH—; and
Y, Y$^a$, Y$^b$ and the radicals R¹⁰ and R¹¹ are as defined above.

Especially worthy of mention are also the compounds of formula II and of formulae IIa to IId wherein
Y$^a$ is hydrogen; or fluorine; and
Y$^b$ is chlorine; or bromine.

Special prominence is to be given to the compounds of formula IIa

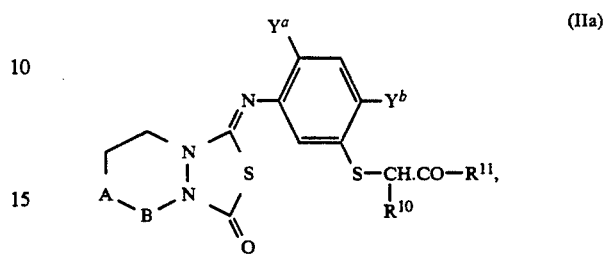
(IIa)

wherein
A-B is —CH₂—CH₂—;
Y$^a$ is hydrogen; or fluorine;
Y$^b$ is chlorine; or bromine;
R¹⁰ is hydrogen; or C₁-C₄alkyl; and
R¹¹ is C₁-C₄alkoxy; C₅-C₆cycloalkyloxy; C₃-C₆alkenyloxy; C₃-C₆alkynyloxy; C₁-C₄alkylthio; or C₁-C₄alkoxycarbonyl-C₁-C₄alkoxy.

The invention relates especially to the combination of the compounds of formula IIa to which special prominence was given with the above-mentioned especially preferred sulfonylureas of formula Ia.

The compounds of Tables 7 and 8 may be mentioned as especially preferred individual compounds:

TABLE 7

As compounds of formula IIa:

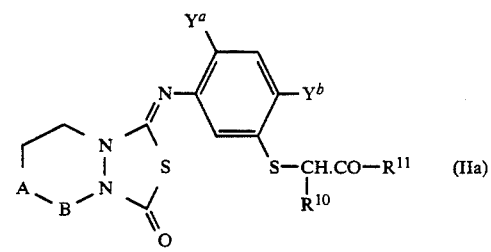
(IIa)

| Comp. No. | A—B | Y$^a$ | Y$^b$ | R¹⁰ | R¹¹ |
|---|---|---|---|---|---|
| 7.001 | —CH₂—CH₂— | H | Cl | CH₃ | O—C₂H₅ |
| 7.003 | —CH₂—CH₂— | F | Cl | CH₃ | O—C₂H₅ |
| 7.004 | —CH₂—CH₂— | F | Cl | C₃H₇ | O—C₂H₅ |
| 7.005 | —CH₂—CH₂— | F | Cl | H | O—C₂H₅ |
| 7.006 | —CH₂—CH₂— | F | Cl | CH₃ | O—CH₂CH₂OCH₃ |
| 7.007 | —CH₂—CH₂— | H | Cl | H | O—C₂H₅ |
| 7.008 | —CH₂—CH₂— | H | Cl | H | O-cyclo-C₅H₉ |
| 7.009 | —CH₂—CH₂— | H | Cl | CH₃ | O—CH₂CH₂OCH₃ |
| 7.010 | —CH₂—CH₂— | H | Cl | C₄H₉ | O—C₂H₅ |
| 7.011 | —CH₂—CH₂— | H | Cl | C₃H₇ | O-cyclo-C₅H₉ |
| 7.012 | —CH₂—CH₂— | F | Cl | H | O—CH₃ |
| 7.013 | —CH₂—CH₂— | H | Cl | C₂H₅ | O—CH₃ |
| 7.014 | —CH₂—CH₂— | H | Cl | C₄H₉ | O—CH₃ |
| 7.015 | —CH₂—CH₂— | F | Cl | H | O—C₃H₇ |
| 7.016 | —CH₂—CH₂— | F | Cl | H | O-(i)-C₃H₇ |
| 7.017 | —CH₂—CH₂— | F | Cl | H | O-(i)-C₄H₉ |
| 7.018 | —CH₂—CH₂— | F | Cl | H | O-(i)-C₅H₁₁ |
| 7.019 | —CH₂—CH₂— | H | Cl | H | O-cyclo-C₆H₁₁ |
| 7.020 | —CH₂—CH₂— | F | Cl | H | O-cyclo-C₆H₁₁ |
| 7.021 | —CH₂—CH₂— | H | Cl | H | O—CH₂CH₂OCH₃ |
| 7.022 | —CH₂—CH₂— | H | Cl | H | O—CH₂CH₂OCH₃ |
| 7.023 | —CH₂—CH₂— | H | Cl | H | O—CH₂CH(CH₃)C₂H₅ |
| 7.024 | —CH₂—CH₂— | F | Cl | H | O—CH₂CH(CH₃)C₂H₅ |
| 7.025 | —CH₂—CH₂— | F | Cl | H | O—CH₂CH₂—O—C₄H₉ |
| 7.026 | —CH₂—CH₂— | H | Cl | CH₃ | O—CH₃ |

TABLE 7-continued

As compounds of formula IIa:

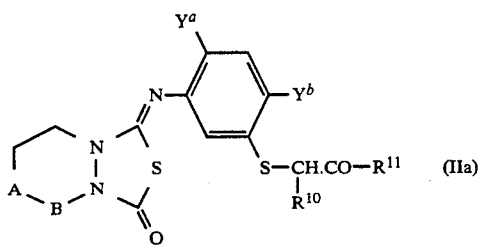

| Comp. No. | A—B | $Y^a$ | $Y^b$ | $R^{10}$ | $R^{11}$ |
|---|---|---|---|---|---|
| 7.027 | —CH₂—CH₂— | F | Cl | CH₃ | O—CH₃ |
| 7.028 | —CH=CH— | H | Cl | CH₃ | O—C₂H₅ |
| 7.029 | —CH=CH— | F | Cl | CH₃ | O—C₂H₅ |
| 7.030 | —CH=CH— | F | Cl | CH₃ | O—C₂H₅ |
| 7.031 | —CH=CH— | F | Cl | CH₃ | O—C₂H₅ |
| 7.032 | —CH=CH— | F | Cl | C₃H₇ | O—C₂H₅ |
| 7.033 | —CH=CH— | F | Cl | H | O—C₂H₅ |
| 7.034 | —CH=CH— | F | Cl | CH₃ | O—CH₂CH₂OCH₃ |
| 7.035 | —CH=CH— | H | Cl | H | O—C₂H₅ |
| 7.036 | —CH=CH— | H | Cl | H | O-cyclo-C₅H₉ |
| 7.037 | —CH=CH— | H | Cl | CH₃ | O—CH₂CH₂OCH₃ |
| 7.038 | —CH=CH— | H | Cl | C₄H₉ | O—C₂H₅ |
| 7.039 | —CH=CH— | H | Cl | C₃H₇ | O-cyclo-C₅H₉ |
| 7.040 | —CH=CH— | F | Cl | H | O—CH₃ |
| 7.041 | —CH=CH— | H | Cl | C₂H₅ | O—CH₃ |
| 7.042 | —CH=CH— | H | Cl | C₄H₉ | O—CH₃ |
| 7.043 | —CH=CH— | F | Cl | H | O—C₃H₇ |
| 7.044 | —CH=CH— | F | Cl | H | O-(i)-C₃H₇ |
| 7.045 | —CH=CH— | F | Cl | H | O-(i)-C₄H₉ |
| 7.046 | —CH=CH— | F | Cl | H | O-(i)-C₅H₁₁ |
| 7.047 | —CH=CH— | H | Cl | H | O-cyclo-C₆H₁₁ |
| 7.048 | —CH=CH— | F | Cl | H | O-cyclo-C₆H₁₁ |
| 7.049 | —CH=CH— | H | Cl | H | O—CH₂CH₂OCH₃ |
| 7.050 | —CH=CH— | H | Cl | H | O—CH₂CH₂OCH₃ |
| 7.051 | —CH=CH— | H | Cl | H | O—CH₂CH(CH₃)C₂H₅ |
| 7.052 | —CH=CH— | F | Cl | H | O—CH₂CH(CH₃)C₂H₅ |
| 7.053 | —CH=CH— | F | Cl | H | O—CH₂CH₂—O—C₄H₉ |
| 7.054 | —CH=CH— | H | Cl | CH₃ | O—CH₃ |
| 7.055 | —CH=CH— | F | Cl | CH₃ | O—CH₃ |

TABLE 8

As compounds of formulae IIb–IId:

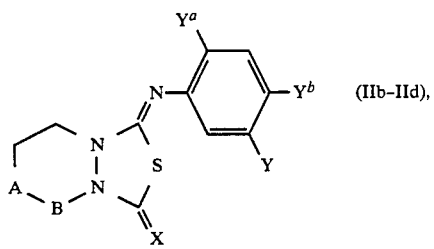

| Comp. No. | A—B | X | $Y^a$ | $Y^b$ | Y |
|---|---|---|---|---|---|
| 8.001 | —CH₂—CH— | O | H | Cl | —OCH₃ |
| 8.002 | —CH₂—CH₂— | O | H | Cl | —OCH₂H₅ |
| 8.003 | —CH₂—CH₂— | O | H | Cl | —OCH₂CH=CH₂ |
| 8.004 | —CH₂—CH₂— | O | H | Cl | —OCH₂—C≡CH |
| 8.005 | —CH₂—CH₂— | O | H | Cl | —O-cyclo-C₅H₁₁ |
| 8.006 | —CH₂—CH₂— | O | H | Cl | —O—C₆H₅ |
| 8.007 | —CH₂—CH₂— | O | H | Br | —OCH₃ |
| 8.008 | —CH₂—CH₂— | O | H | Br | —O—CH₂C≡CH |
| 8.009 | —CH₂—CH₂— | O | F | Cl | —O-(i)C₃H₇ |
| 8.010 | —CH₂—CH₂— | O | F | Cl | —O—CH₂CH=CH₂ |
| 8.011 | —CH₂—CH₂— | O | F | Cl | —O—CH—C≡CH |
| 8.012 | —CH₂—CH₂— | O | F | Cl | —O—CH₂—C₆H₅ |
| 8.013 | —CH₂—CH₂— | O | F | Cl | —O—C₆H₅ |
| 8.014 | —CH₂—CH₂— | O | Cl | Cl | —O-(i)C₃H₇ |
| 8.015 | —CH₂—CH₂— | O | Cl | Cl | —O—C₆H₅ |
| 8.016 | —CH₂—CH₂— | S | F | Cl | —O-(i)-C₃H₇ |

TABLE 8-continued

As compounds of formulae IIb–IId:

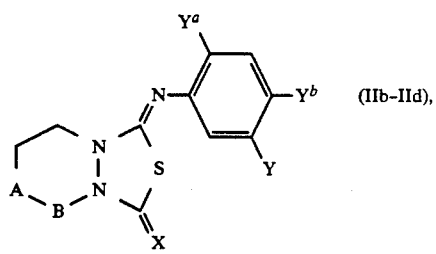

(IIb-IId)

| Comp. No. | A—B | X | $Y^a$ | $Y^b$ | Y |
|---|---|---|---|---|---|
| 8.017 | —CH₂—CH₂— | S | F | Cl | —O—C₆H₅ |
| 8.018 | —CH₂—CH₂— | O | F | Cl | —COSCH(CH₃)COOCH₂CH₂OC₂H₅ |
| 8.019 | —CH₂—CH₂— | O | F | Cl | —O-(s)C₄H₉ |
| 8.020 | —CH₂—CH₂— | O | H | Cl | —O-(n)C₅H₁₁ |
| 8.021 | —CH₂—CH₂— | O | H | Br | —O-(i)C₃H₇ |
| 8.022 | —CH₂—CH₂— | O | H | Cl | —O—C₂H₅—CH=CH₂ |
| 8.023 | —CH₂—CH₂— | O | H | Cl | —O—CH₂C(CH₃)=CH₃ |
| 8.024 | —CH₂—CH₂— | O | H | Br | —O—CH₂CH=CH₂ |
| 8.025 | —CH₂—CH₂— | O | H | Cl | —O—CH₂CH=C(CH₃)₂ |
| 8.026 | —CH₂—CH₂— | O | H | Cl | —SC₂H₅ |
| 8.027 | —CH₂—CH₂— | O | H | Cl | —SO₂C₂H₅ |
| 8.028 | —CH₂—CH₂— | O | H | Cl | —SCH₂CH=CH₂ |
| 8.029 | —CH₂—CH₂— | O | H | Cl | —SCH₂—C≡CH |
| 8.030 | —CH₂—CH₂— | O | H | Cl | —CH₂CN |
| 8.031 | —CH₂—CH₂— | O | H | Cl | —COO—C₆H₅ |
| 8.032 | —CH₂—CH₂— | O | H | Cl | —COO—CH₂—C₆H₅ |
| 8.033 | —CH₂—CH₂— | O | F | Cl | —COOH |
| 8.034 | —CH₂—CH₂— | O | F | Cl | —COO-(i)C₃H₇ |
| 8.035 | —CH₂—CH₂— | O | F | Cl | —COO—CH₃ |
| 8.036 | —CH₂—CH₂— | O | H | Cl | —COO-(cyclo)C₅H₁₁ |
| 8.037 | —CH₂—CH₂— | O | H | Cl | —COSC₂H₅ |
| 8.038 | —CH₂—CH₂— | O | F | H | —COO—C₂H₅ |
| 8.039 | —CH₂—CH₂— | O | H | Cl | —CO₂—CH(CH₃)—CO₂—C₂H₅ |
| 8.040 | —CH₂—CH₂— | O | H | Cl | —CO₂—C₂H₄—OCH₃ |
| 8.041 | —CH₂—CH₂— | O | Cl | Cl | —COOC₂H₅ |
| 8.042 | —CH₂—CH₂— | O | F | F | —COOCH₃ |
| 8.043 | —CH₂—CH₂— | O | F | F | —COOC₂H₅ |
| 8.044 | —CH₂—CH₂— | O | H | Cl | —COOC₂H₅ |
| 8.045 | —CH₂—CH₂— | O | H | Cl | —COO-(i)C₃H₇ |
| 8.046 | —CH₂—CH₂— | O | H | Cl | —OCH(CH₃)COO—C₂H₅ |
| 8.047 | —CH₂—CH₂— | O | H | Cl | —OCH₂COO—C₂H₅ |
| 8.048 | —CH₂—CH₂— | O | F | Cl | —OCH(CH₃)COO—C₂H₅ |
| 8.049 | —CH₂—CH₂— | O | F | Cl | —OCH₂COO—C₂H₅ |
| 8.050 | —CH₂—CH₂— | O | H | Cl | —OCH(CH₃)COO—CH₂C≡CH |
| 8.051 | —CH₂—CH₂— | O | H | Cl | —OCH(CH₃)COO—CH₂—C₆H₅ |
| 8.052 | —CH₂—CH₂— | O | H | Cl | —OCH(CH₃)COS—C₂H₅ |
| 8.053 | —CH₂—CH₂— | O | H | Cl | —OCH(CH₃)COO-(i)C₄H₉ |
| 8.054 | —CH₂—CH₂— | O | H | Cl | —OCH(CH₃)COO—C₂H₄—O—CH₃ |
| 8.055 | —CH₂—CH₂— | O | H | Cl | —OCH(CH₃)COO-(cyclo)C₆H₁₁ |
| 8.056 | —CH₂—CH₂— | O | Cl | Cl | —OCH(CH₃)COO—C₂H₅ |
| 8.057 | —CH₂—CH₂— | O | F | Cl | —OCH(CH₃)COO—CH₃ |
| 8.058 | —CH₂—CH₂— | O | F | Cl | —OCH(CH₃)COO-(i)C₃H₇ |
| 8.059 | —CH₂—CH₂— | O | F | Cl | —OCH(CH₃)COO—CH₂—C≡CH |
| 8.060 | —CH₂—CH₂— | O | F | Cl | —OCH(CH₃)COO—C₂H₄—CH₃ |
| 8.061 | —CH₂—CH₂— | O | F | Cl | —OCH(CH₃)COO—C₂H₄—O-(n)C₄H₉ |
| 8.062 | —CH₂—CH₂— | O | F | Cl | —OCH(CH₃)COO—CH(CH₃)CH₂OCH₃ |
| 8.063 | —CH₂—CH₂— | O | F | Cl | —OCH(CH₃)COO—CH₂—COOC₂H₅ |
| 8.064 | —CH₂—CH₂— | O | F | Cl | —OCH(CH₃)COO—CH(CH₃)—COOCH₃ |
| 8.065 | —CH=CH— | O | H | Cl | —OCH₃ |
| 8.066 | —CH=CH— | O | H | Cl | —OC₂H₅ |
| 8.067 | —CH=CH— | O | H | Cl | —OCH₂CH=CH₂ |
| 8.068 | —CH=CH— | O | H | Cl | —OCH₂—C≡CH |
| 8.069 | —CH=CH— | O | H | Cl | —O-cyclo-C₅H₁₁ |
| 8.070 | —CH=CH— | O | H | Cl | —O—C₆H₅ |
| 8.071 | —CH=CH— | O | H | Br | —OCH₃ |
| 8.072 | —CH=CH— | O | H | Br | —O—CH₂C≡CH |
| 8.073 | —CH=CH— | O | F | Cl | —O-(i)C₃H₇ |
| 8.074 | —CH=CH— | O | F | Cl | —O—CH₂CH=CH₂ |
| 8.075 | —CH=CH— | O | F | Cl | —O—CH—C≡CH |
| 8.076 | —CH=CH— | O | F | Cl | —O—CH₂—C₆H₅ |
| 8.077 | —CH=CH— | O | F | Cl | —O—C₆H₅ |
| 8.078 | —CH=CH— | O | Cl | Cl | —O-(i)C₃H₇ |
| 8.079 | —CH=CH— | O | Cl | Cl | —O—C₆H₅ |
| 8.080 | —CH=CH— | S | F | Cl | —O-(i)-C₃H₇ |
| 8.081 | —CH=CH— | S | F | Cl | —O—C₆H₅ |
| 8.082 | —CH=CH— | S | Cl | Cl | —O-(i)C₃H₇ |

TABLE 8-continued

As compounds of formulae IIb–IId:

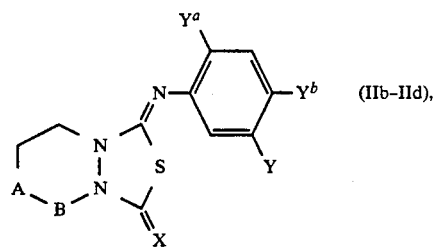

(IIb–IId),

| Comp. No. | A—B | X | $Y^a$ | $Y^b$ | Y |
|---|---|---|---|---|---|
| 8.083 | —CH=CH— | O | F | Cl | —O-(s)$C_4H_9$ |
| 8.084 | —CH=CH— | O | H | Cl | —O-(n)$C_5H_{11}$ |
| 8.085 | —CH=CH— | O | H | Br | —O-(i)$C_3H_7$ |
| 8.086 | —CH=CH— | O | H | Cl | —O—$C_2H_5$—CH=$CH_2$ |
| 8.087 | —CH=CH— | O | H | Cl | —O—$CH_2C(CH_3)$=$CH_3$ |
| 8.088 | —CH=CH— | O | H | Br | —O—$CH_2CH$=$CH_2$ |
| 8.089 | —CH=CH— | O | H | Cl | —O—$CH_2CH$=$C(CH_3)_2$ |
| 8.090 | —CH=CH— | O | H | Cl | —S$C_2H_5$ |
| 8.091 | —CH=CH— | O | H | Cl | —$SO_2C_2H_5$ |
| 8.092 | —CH=CH— | O | H | Cl | —S$CH_2CH$=$CH_2$ |
| 8.093 | —CH=CH— | O | H | Cl | —S$CH_2$—C≡CH |
| 8.094 | —CH=CH— | O | H | Cl | —$CH_2CN$ |
| 8.095 | —CH=CH— | O | H | Cl | —COO—$C_6H_5$ |
| 8.096 | —CH=CH— | O | H | Cl | —COO—$CH_2$—$C_6H_5$ |
| 8.097 | —CH=CH— | O | F | Cl | —COOH |
| 8.098 | —CH=CH— | O | F | Cl | —COO—(i)$C_3H_7$ |
| 8.099 | —CH=CH— | O | F | Cl | —COO—$CH_3$ |
| 8.100 | —CH=CH— | O | H | Cl | —COO-(cyclo)$C_5H_{11}$ |
| 8.101 | —CH=CH— | O | H | Cl | —COS$C_2H_5$ |
| 8.102 | —CH=CH— | O | F | H | —COO—$C_2H_5$ |
| 8.103 | —CH=CH— | O | H | Cl | —$CO_2$—$CH(CH_3)$—$CO_2$—$C_2H_5$ |
| 8.104 | —CH=CH— | O | H | Cl | —$CO_2$—$C_2H_4$—$OCH_3$ |
| 8.105 | —CH=CH— | O | Cl | Cl | —COO$C_2H_5$ |
| 8.106 | —CH=CH— | O | F | F | —COO$CH_3$ |
| 8.107 | —CH=CH— | O | F | F | —COO$C_2H_5$ |
| 8.108 | —CH=CH— | O | H | Cl | —COO$C_2H_5$ |
| 8.109 | —CH=CH— | O | H | Cl | —COO-(i)$C_3H_7$ |
| 8.110 | —CH=CH— | O | H | Cl | —OCH($CH_3$)COO—$C_2H_5$ |
| 8.111 | —CH=CH— | O | H | Cl | —O$CH_2$COO—$C_2H_5$ |
| 8.112 | —CH=CH— | O | F | Cl | —OCH($CH_3$)COO—$C_2H_5$ |
| 8.113 | —CH=CH— | O | F | Cl | —O$CH_2$COO—$C_2H_5$ |
| 8.114 | —CH=CH— | O | H | Cl | —OCH($CH_3$)COO—$CH_2$C≡CH |
| 8.115 | —CH=CH— | O | H | Cl | —OCH($CH_3$)COO—$CH_2$—$C_6H_5$ |
| 8.116 | —CH=CH— | O | H | Cl | —OCH($CH_3$)COS—$C_2H_5$ |
| 8.117 | —CH=CH— | O | H | Cl | —OCH($CH_3$)COO-(i)$C_4H_9$ |
| 8.118 | —CH=CH— | O | H | Cl | —OCH($CH_3$)COO—$C_2H_4$—O—$CH_3$ |
| 8.119 | —CH=CH— | O | H | Cl | —OCH($CH_3$)COO-(cyclo)$C_6H_{11}$ |
| 8.120 | —CH=CH— | O | Cl | Cl | —OCH($CH_3$)COO—$C_2H_5$ |
| 8.121 | —CH=CH— | O | F | Cl | —OCH($CH_3$)COO—$CH_3$ |
| 8.122 | —CH=CH— | O | F | Cl | —OCH($CH_3$)COO-(i)$C_3H_7$ |
| 8.123 | —CH=CH— | O | F | Cl | —OCH($CH_3$)COO—$CH_2$—C≡CH |
| 8.124 | —CH=CH— | O | F | Cl | —OCH($CH_3$)COO—$C_2H_4$—O—$CH_3$ |
| 8.125 | —CH=CH— | O | F | Cl | —OCH($CH_3$)COO—$C_2H_4$—O-(n)$C_4H_9$ |
| 8.126 | —CH=CH— | O | F | Cl | —OCH($CH_3$)COO—CH($CH_3$)$CH_2OCH_3$ |
| 8.127 | —CH=CH— | O | F | Cl | —OCH($CH_3$)COO—$CH_2$—COO$C_2H_5$ |
| 8.128 | —CH=CH— | O | F | Cl | —OCH($CH_3$)COO—CH($CH_3$)—COO$CH_3$ |

Special prominence is to be given to the combination of compounds of formula I with N-[2-(2-fluoroethylthio)phenylsulfonyl]-N'-(4-methoxy-6-methyl-1,3,5-triazin-2-yl)-urea, N-[2-(3,3,3-trifluoropropyl)phenylsulfonyl]-N'-(4-methoxy-6-methyl-1,3,5-triazin-2-yl)-urea, N-[2-(3,3-difluorobut-l-enyl)phenylsulfonyl]-N'-(4-methoxy-6-methyl-1,3,5-triazin-2-yl)-urea, N-[2-($,3-difluorobutyl)phenylsulfonyl]-N'-(4-methoxy-6-methyl-1,3,5-triazin-2-yl)-urea, N-[2-(2,2-difluoroethylthio)-phenylsulfonyl]-N'-(4-methoxy-6-methyl-1,3,5-triazin-2-yl)-urea, N-[2-(2-methoxyethoxy)phenylsulfonyl]-N'-(4,6-dimethoxy- 1,3,5-triazin-2-yl)-urea, N-[3-dimethylaminocarbonylpyridin-2-sulfonyl]-N'-(4,6-dimethoxypyrimidin-2-yl)-urea, N-[3-ethylsulfonylpyridin-2-sulfonyl]-N'-(4,6-dimetboxypyrimidin-2-yl)-urea, N-[2-methoxycarbonylphenylsulfonyl]-N'-(4,6-bis-difluoromethoxypyrimidin-2-yl)-urea, N-[2-methoxycarbonylphenylsulfonyl]-N'-(4,6-dimethoxypyrimidin-2-yl)-urea, N-[2-methoxycarbonylbenzylsulfonyl]-N'-(4,6-dimethoxypyrimidin-2-yl)-urea, N-[2-methoxycarbonylphenylsulfonyl]-N'-methyl-N"(4-methoxy-6-methyl-1,3,5-triazin-2-yl)-urea, N-[1-methyl-4-ethoxycarbonylpyr4zol-5-sulfonyl]-N'-(4,6-dimethoxypyrimidin-2-yl)-urea, or N-[2-(2-chloroetholoxy)-phenylsulfonyl]-N'-(4-methoxy-6-methyl-1,3,5-triazin-2-yl)-urea as compound of formula la together with a synergistically effective amount of 3-[(4-chloro-2-fluoro-5-methoxycarbonylmethylthio)phenyliminol-5,6,7,8-tetrahydro-1H,3H-(I,3,4)-thiadiazolo[3,4- a]pyridazine (compound 7.012) as compound of formula IIa.

Special prominence is also to be given to the combination of compounds of formula I with N-[2-(oxetan-3-yloxycarbonyl)phenylsulfonyl]-N'-(4methoxy-6-methyl-1,3,5-triazin-2-yl)-urea (compound 1.041) as compound of formula Ia together with a synergistically effective amount of 3-[(4-chloro-2-fluoro-5-methoxycarbonylmethylthio)phenylimino] -5,6,7,8-tetrahydro-1H,3H-(I,3,4)-thiadiazolo[3,4-a]pyridazine (compound 7.012) as compound of formula IIa.

Special prominence is likewise to be given to the combination of compounds of formula I with N-[2-(2-fluoroethylthio)phenylsulfonyl]-N'-(4-methoxy-6-methyl-1,3,5-triazin-2-yl)-urea, N-[2-(3,3,3-trifluoropropyl)-phenylsulfonyl]-N'-(4-methoxy-6-methyl-1,3,5-triazin-2-yl)-urea, N-[2-(3,3-difluorobut-1-enyl)phenylsulfonyl]-N'-(4-methoxy-6-methyl-1,3,5-triazin-2-yl)-urea, N-[2-(3,3-difluorobutyl)phenylsulfonyl]-N'-(4-methoxy-6-methyl-1,3,5-triazin-2-yl)-urea, N-[2-(2,2-difluoroethylthio)phenylsulfonyl]-N'-(4-methoxy-6-methyl-1,3,5-triazin-2-yl)-urea, N-[2-(2-methoxyethoxy)phenylsulfonyl]-N'-(4,6-dimethoxy-1,3,5-triazin-2-yl)-urea, N-[3-dimethylaminocarbonylpyridin-2-sulfonyl]-N'-(4,6-dimethoxypyrimidin-2-yl)-urea, N-[3-ethylsulfonylpyridin-2-sulfonyl]-N'-(4,6-dimethoxypyrimidin-2-yl)-urea, N-[2-methoxycarbonylphenylsulfonyl]-N'-(4,6-bis-difluoromethoxypyrimidin-2-yl)-urea, N-[2-methoxycarbonylphenylsulfonyl]-N'-(4,6-dimethoxypyrimidin-2-yl)-urea, N-[2-methoxycarbonylbenzylsulfonyl]-N'-(4,6-dimethoxypylimidin-2-yl)-urea, N-[2-methoxycarbonylphenylsulfonyl]-N'-methyl-N'-(4-methoxy-6-methyl-1,3,5-triazin-2-yl)-urea, N-[I-methyl-4-ethoxycarbonylpyrazol-5-sulfonyl]-N'-(4,6-dimethoxypyrimidin-2-yl)-urea, or N-[2-(2-chloroethoxy)phenylsulfonyl]-N'-(4-methoxy-6-methyl-1,3,5-triazin-2-yl)-urea as compound of formula Ia together with a synergistically effective amount of 9-[4-chloro-2-fluoro-5-(2-ethoxyethoxycarbonyl-1-ethylthiocarbonyl)-phenylimino]-S-diazabicyclo[4.3.0]nonan-7-one (compound 8.018) as compound of formula IIa.

Special prominence is also to be given to the combination of compounds of formula I with N-[2-(oxetan-3-yloxycarbonyl)phenylsulfonyl]-N'-(4-methoxy-6-methyl-1,3,5-triazin-2-yl)-urea (compound 1.041) as compound of formula Ia together with a synergistically effective amount of 9-[4-chloro-2-fluoro-5-(2-ethoxyethoxycarbonyl-1-ethylthiocarbonyl)phenylimino]-8-diazabicyclo[4.3.0]nonan-7-one (compound 8.018) as compound of formula IIa.

Very special prominence is to be given to the combination of compounds of formula I with N-[2-(2-chloroethoxy)phenylsulfonyl]-N'-(4-methoxy-6-methyl-1,3,5-triazin-2-yl)-urea as compound of formula Ia together with a synergistically effective amount of 3-[(4-chloro-2-fluoro-5-methoxycarbonylmethylthio)phenyliminol-5,6,7,8-tetrahydro-1H,3H-(I,3,4)-thiadiazolo[3,4-pyridazine as compound of formula IIa; or to the combination with N-[2-(2-chloroethoxy)phenylsulfonyl]-N'-(4-methoxy-6-methyl-1,3,5-triazin-2-yl)-urea as compound of formula Ia together with a synergistically effective amount of 9-[4-chloro-2-fluoro-5-(2-ethoxyethoxycarbonyl-1-ethylthiocarbonyl)phenylimino]-8-diazabicyclo[4.3.0]nonan-7-one as compound of formula IIa.

Very special prominence is also to be given to the combination of compounds of formula I with N-[2-(oxetan-3-yloxycarbonyl)phenylsulfonyl]-N'-(4-methoxy-6-methyl-1,3,5-triazin-2-yl)-urea (compound 1.041) as compound of formula Ia together with a synergistically effective amount of 3-[(4-chloro-2-fluoro-5-methoxycarbonylmethylthio)phenyliminol-5,6,7,8-tetrahydro-1H,3H-(I,3,4)-thiadiazolo[3,4-a]pyridazine (compound 7.012) as compound of formula IIa.

The mixture of the compounds of formulae I and 11 exhibits synergistic, that is to say, superadditive, selective herbicidal action in a wide range of mixing ratios. It can be used advantageously in crops of useful plants against a large number of agronomically important weeds, such as the weeds Veronica, Galium, Papaver, Solanum, Chenopodium, Amaranthus, Xanthium, Abutilon, Ambrosia, Sagritharia and Ipomoea.

The herbicidal mixture according to the invention can be used advantageously in the control of weeds in the following crops of useful plants: cereals (wheat, barley, rye, sorghum, oats), rice, maize or soybeans. The crops wheat, barley and maize are to be given special mention.

The mixing ratio of the two herbicidal components of formulae I and II at which the synergistic herbicidal action occurs can be ascertained by tests. In the mixture according to the invention, the ratio by weight of the compound of formula I to the compound of formula 11 is preferably from 1:0. 1 to 1:20. From 1: 1 to 1: 10; especially from 1:3 to 1:6, is especially preferred in cereals. In maize, the ratio by weight is preferably in the range of from 1: 0. 1 to 1: 1.

The rate of application can vary within a wide range and depends on the nature of the soil, the type of application (pre- or postemergence; seed dressing; application to the seed furrow; no tillage application, etc.), on the cultivated plant, the weed to be controlled, the prevailing climatic conditions and on other factors determined by the type of application, the time of application and the target crop. In general, the active ingredient mixture according to the invention can be used at a rate of application of from 1 to 500 [g active ingredient-/ha], especially from I to 100 [g active ingredient/ha]. The herbicidal mixture according to the invention is preferably used postemergence.

The mixture of compounds of formulae I and II is used in unmodified form, as obtainable from synthesis, or, preferably, together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures containing the compounds (active ingredients) of formulae I and 11 and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons such as paraffins, cyclohexane or tetrahydronaphthalene; alcohols such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, also silicone oils.

The solid carriers used, e.,. for dusts and dispersible powders, are normally natural mineral fillers such as calcite, talcum, kaolin, montmofillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$-$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain I to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described inter alia in the following publications:

"Mc Cutcheon's Detergents and Emulsifiers Annual", Mc Publishing Corp., Glen Rock, N.J., 1988.

M. and J. Ash, "Encyclopedia of Surfactants", Vol. I-III, Chemical Publishing Co., New York, 1980-1981.

Dr. Helmut Stache "Tensid-Taschenbuch", Carl Hanser Verlag, Munich/Vienna 1981.

The herbicidal compositions generally comprise 0. I to 99 %, preferably 0. 1 to 95 %, of a compound of formula 1, I to 99 % of a solid or liquid adjuvant and 0 to 25 %, preferably 0.1 to 25 %, of a surfactant.

Whereas commercial products will preferably be formulated as concentrates, the end user will normally employ dilute formulations.

The compositions may also comprise further additives such as stabilisers, for example vegetable oils and epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

Preferred formulations are composed in particular of the following constituents (throughout, percentages are by weight):

| Emulsifiable concentrates: | |
| --- | --- |
| active ingredient mixture: | 1 to 90%, preferably 5 to 20% |
| surfactant: | 1 to 30%, preferably 10 to 20% |
| liquid carrier: | 5 to 94%, preferably 70 to 85% |
| Dusts: | |
| active ingredient mixture: | 0.1 to 10%, preferably 0.1 to 1% |
| solid carrier: | 99.9 to 90%, preferably 99.9 to 99% |
| Suspension concentrates: | |
| active ingredient mixture: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient mixture: | 0.5 to 90%, preferable 1 to 80% |
| surfactant: | 0.5 to 20%, preferably 1 to 15% |
| solid carrier: | 5 to 95%, preferably 15 to 90% |
| Granules: | |
| active ingredient mixture: | 0.5 to 30%, preferably 3 to 15% |

-continued

| solid carrier: | 99.5 to 70%, preferably 97 to 85% |

BIOLOGICAL EXAMPLES

A synergistic effect exists whenever the action of the active ingredient combination I and II is greater than the sum of the action of the active ingredients applied individually.

The herbicidal action to be expected Ae for a given combination of two herbicides can be calculated (see COLBY, S. R., "Calculating synergistic and antagonistic response of herbicide combinations", Weeds 15, pages 20–22, 1967) as follows:

$$Ae = X + \frac{Y \cdot (100 - X)}{100}$$

in which:
- X = percentage growth inhibition in the case of treatment with a compound of formula I at a rate of application of p kg per hectare in comparison with the untreated control (=0 %).
- Y = percentage herbicidal action in the case of treatment with a compound of formula I or II at a rate of application of q kg per hectare in comparison with the untreated control.
- Ae = expected herbicidal action (percentage growth inhibition in comparison with the untreated control) after treatment with the compounds of formulae I and II at a rate of application of p +q kg of active ingredient per hectare.

If the action actually observed is greater than the value to be expected Ae, synergism exists.

The synergistic effect of the combinations of compounds I and 11 is demonstrated in the following Examples.

B. Synergistic herbicidal action in wheat, maize, cereals, soybeans and lice

The active ingredients are applied by means of a small-plot spray device with a water volume of 500 l/ha to emergent broad-leaved weeds in wheat crops. The corresponding amounts to be applied are weighed out separately for each plot to be treated individually. After application, evaluation is made in respect of the tolerance of the cultivated plant and the action on the weeds after the time intervals indicated in the Examples (Tables 1 to 19). The percentage reduction of the biomass is recorded in comparison with the untreated control. A scale of percentages from 0 % (as untreated control) to 100 % (plants withered) is used as a standard. Assessment is made at intervals of 10 % in the lower range of action and at smaller intervals in the upper range of activity.

The results of the comparison are recorded in Tables I and 2 together with the expected values calculated in accordance with the Colby formula. The compounds used in each case and the rates of application as well as the tested cultivated plants and weeds are indicated.

The individual Tables are as follows:
Table 1: Test in winter wheat of the Gamil variety
Table 2: Test in winter wheat of the Ares variety
Tables 3 to 7: Tests in maize
Tables 8 to 1 1: Tests in cereals
Table 12: Test in soybeans
Tables 13 to 18: Tests in rice
Table 19: Test in maize

TABLE 1

| Comp. No. | Evaluation Days after appl. | Myosotis arv. 37 | | 66 | | Papaver rho 37 | | 66 | | Viola tri 37 | | 66 | |
|---|---|---|---|---|---|---|---|---|---|---|---|---|---|
| 1.001 | [g ai/ha] | | | | | | | | | | | | |
| | 5 | 40 | | 60 | | 30 | | 40 | | 40 | | 50 | |
| | 7.5 | 80 | | 80 | | 70 | | 70 | | 40 | | 60 | |
| | 15 | 80 | | 80 | | 70 | | 90 | | 70 | | 70 | |
| 7.012 | [g ai/ha] | | | | | | | | | | | | |
| | 15 | 30 | | 75 | | 50 | | 50 | | 70 | | 40 | |
| | 30 | 60 | | 60 | | 70 | | 80 | | 70 | | 50 | |
| comb. | [g ai/ha] | | | | | | | | | | | | |
| 1.001 | 5 + 15 | 80 | 58* | 94 | 90* | 85 | 65* | 85 | 75* | 75 | 82* | 70 | 70* |
| and | +30 | 100 | 76* | 96 | 84* | 96 | 79* | 100 | 88* | 94 | 82* | 85 | 75* |
| 7.012 | 7.5 + 15 | 92 | 86* | 96 | 95* | 85 | 85* | 97 | 85* | 85 | 82* | 80 | 76* |
| | +30 | 100 | 92* | 100 | 92* | 100 | 91* | 100 | 94* | 94 | 82* | 90 | 80* |
| | 15 + 30 | 100 | 92* | 100 | 92* | 100 | 91* | 100 | 98* | 94 | 91* | 94 | 85* |

| Comp. No. | Evaluation Days after appl. | Veronica hed. 37 | | 66 | | Lamium pur. 37 | | 66 | | Stellaria media 37 | | 66 | |
|---|---|---|---|---|---|---|---|---|---|---|---|---|---|
| 1.001 | [g ai/ha] | | | | | | | | | | | | |
| | 5 | 40 | | 60 | | 50 | | 70 | | 50 | | 80 | |
| | 7.5 | 50 | | 70 | | 60 | | 80 | | 80 | | 80 | |
| | 15 | 80 | | 80 | | 85 | | 90 | | 90 | | 94 | |
| 7.012 | [g ai/ha] | | | | | | | | | | | | |
| | 15 | 70 | | 50 | | 50 | | 70 | | 60 | | 60 | |
| | 30 | 80 | | 60 | | 60 | | 85 | | 70 | | 75 | |
| comb. | [g ai/ha] | | | | | | | | | | | | |
| 1.001 | 5 + 15 | 80 | 82* | 85 | 80* | 90 | 75* | 80 | 91* | 85 | 80* | 90 | 92* |
| and | +30 | 96 | 88* | 94 | 84* | 100 | 80* | 95 | 96* | 90 | 85* | 90 | 95* |
| 7.012 | 7.5 + 15 | 92 | 85* | 92 | 85* | 94 | 90* | 90 | 94* | 92 | 92* | 90 | 96* |
| | +30 | 94 | 90* | 96 | 88* | 100 | 84* | 100 | 97* | 100 | 94* | 90 | 98* |
| | 15 + 30 | 94 | 96* | 98 | 92* | 100 | 94* | 100 | 98* | 99 | 97* | 92 | 98* |

The values marked * correspond to the expected value Ae

TABLE 2

| Comp. No. | Eval. Days after appl. | Galium apa. 19 | | 39 | | Veronica sp. 19 | | 39 | |
|---|---|---|---|---|---|---|---|---|---|
| 1.001 | [g ai/ha] | | | | | | | | |
| | 5 | 35 | | 40 | | 35 | | 40 | |
| | 7.5 | 50 | | 50 | | 50 | | 50 | |
| | 15 | 60 | | 85 | | 60 | | 80 | |
| 7.012 | [g ai/ha] | | | | | | | | |
| | 15 | 30 | | 0 | | 10 | | 0 | |
| | 30 | 30 | | 25 | | 40 | | 25 | |
| comb. 1.001 and 7.012 | [g ai/ha] | | | | | | | | |
| | 5 + 15 | 50 | 54* | 50 | 40* | 50 | 42* | 70 | 40* |
| | +30 | 85 | 68* | 70 | 55* | 85 | 61* | 88 | 55* |
| | 7.5 + 15 | 75 | 65* | 50 | 50* | 80 | 55* | 75 | 50* |
| | +30 | 90 | 75* | 70 | 62* | 88 | 70* | 88 | 62* |
| | 15 + 30 | 90 | 85* | 80 | 89* | 85 | 76* | 90 | 85* |

The values marked * correspond to the expected value Ae

TABLE 3

| Compound No. | [g ai/ha] | Xanthium canadense |
|---|---|---|
| 1.003 | 10 | 35 |
| 7.012 | 10 | 30 |
| comb. 1.003 and 7.012 | 10 + 10 | 70 49* |

The values marked * correspond to the expected value Ae

TABLE 4

| Compound No. | [g ai/ha] | Xanthium canadense |
|---|---|---|
| 2.001 | 30 | 15 |
| 7.012 | 10 | 30 |
| comb. 2.001 and 7.012 | 30 + 10 | 75 40* |

The values marked * correspond to the expected value Ae

TABLE 5

| Compound No. | [g ai/ha] | Ipomoea purpurea |
|---|---|---|
| 1.017 | 30 | 25 |
| 7.012 | 5 | 55 |
| comb. 1.017 and 7.012 | 30 + 5 | 85 66* |

The values marked * correspond to the expected value Ae

TABLE 6

| Compound No. | [g ai/ha] | Ipomoea purpurea |
|---|---|---|
| 2.003 | 30 | 15 |
| 7.012 | 5 | 55 |
| comb. 2.003 and 7.012 | 30 + 5 | 80 62* |

The values marked * correspond to the expected value Ae

TABLE 7

| Compound No. | [g ai/ha] | Amaranthus |
|---|---|---|
| 1.017 | 15 | 75 |
| 8.018 | 5 | 50 |
| comb. 1.017 and 8.018 | 15 + 5 | 96 87* |

The values marked * correspond to the expected value Ae

TABLE 8

| Compound No. | [g ai/ha] | Veronica persica |
|---|---|---|
| 1.001 | 15 | 55 |
| 8.018 | 8 | 55 |
| comb. 1.001 and 8.018 | 15 + 8 | 90 80* |

The values marked * correspond to the expected value Ae

TABLE 9

| Compound No. | [g ai/ha] | Veronica persica |
|---|---|---|
| 6.001 | 15 | 0 |
| 8.018 | 15 | 85 |
| comb. 6.001 and 8.018 | 15 + 15 | 96 85* |

The values marked * correspond to the expected value Ae

TABLE 10

| Compound No. | [g ai/ha] | Chenopodium album |
|---|---|---|
| 1.039 | 2 | 35 |
| 8.018 | 8 | 0 |
| comb. 1.039 and 8.018 | 2 + 8 | 93 35* |

The values marked * correspond to the expected value Ae

TABLE 11

| Compound No. | [g ai/ha] | Chenopodium album |
|---|---|---|
| 1.012 | 4 | 25 |
| 8.018 | 8 | 0 |
| comb. 1.012 and 8.018 | 4 + 8 | 70 25* |

The values marked * correspond to the expected value Ae

TABLE 12

| Compound No. | [g ai/ha] | Chenopodium album |
|---|---|---|
| 1.014 | 30 | 50 |
| 7.012 | 7.5 | 20 |
| comb. 1.014 and 7.012 | 30 + 7.5 | 95 60* |

The values marked * correspond to the expected value Ae

TABLE 13

| Compound No. | [g ai/ha] | Sagitharia |
|---|---|---|
| 1.040 | 5 | 30 |
| 7.012 | 30 | 0 |
| comb. 1.040 and 7.012 | 5 + 30 | 65 30* |

The values marked * correspond to the expected value Ae

TABLE 14

| Compound No. | [g ai/ha] | Sagitharia |
|---|---|---|
| 1.001 | 10 | 65 |
| 7.012 | 30 | 0 |
| comb. 1.001 and | 10 + 30 | 80 65* |

TABLE 14-continued

| Compound No. | [g ai/ha] | Sagitharia |
|---|---|---|
| 7.012 | | |

The values marked * correspond to the expected value Ae

TABLE 15

| Compound No. | [g ai/ha] | Sagitharia |
|---|---|---|
| 4.001 | 5 | 65 |
| 7.012 | 30 | 0 |
| comb. 4.001 and 7.012 | 5 + 30 | 90 65* |

The values marked * correspond to the expected value Ae

TABLE 16

| Compound No. | [g ai/ha] | Sagitharia |
|---|---|---|
| 0.001 | 10 | 65 |
| 8.018 | 30 | 0 |
| comb. 0.001 and 8.018 | 10 + 30 | 85 65* |

The values marked * correspond to the expected value Ae

TABLE 17

| Compound No. | [g ai/ha] | Sagitharia |
|---|---|---|
| 4.001 | 10 | 70 |
| 8.018 | 30 | 0 |
| comb. 4.001 and 8.018 | 5 + 30 | 96 70* |

The values marked * correspond to the expected value Ae

TABLE 18

| Compound No. | [g ai/ha] | Sagitharia |
|---|---|---|
| 1.040 | 10 | 80 |
| 8.018 | 30 | 0 |
| comb. 1.040 and 8.018 | 10 + 30 | 90 80* |

The values marked * correspond to the expected value Ae

TABLE 19

| Compound No. | [g ai/ha] | Amaranthus hybridus |
|---|---|---|
| 1.041 | 15 | 20 |
| 7.012 | 2.5 | 40 |
| comb. 1.041 and 7.012 | 15 + 2.5 | 60 52* |

The values marked * correspond to the expected value Ae

The measured values indicated in Tables 3 to 19 are obtained 3 weeks after application.

F1. Formulation Examples for synergistic active ingredient mixtures
Mixtures of the compounds of formulae I and II
(throughout, percentages are by weight)

| a) Wettable powders | a) | b) | c) | d) |
|---|---|---|---|---|
| Mixture of compounds of formulae I and II | 10% | 20% | 5% | 30% |
| sodium lignosulfonate | 5% | 5% | 5% | 5% |
| sodium laurylsulfate | 3% | — | 3% | — |
| sodium diisobutylnaphthalene-sulfonate | — | 6% | — | 6% |
| octylphenolpolyethylene glycol ether (7-8 mol of ethylene oxide) | — | 2% | — | 2% |
| highly dispersed silicic acid | 5% | 27% | 5% | 27% |
| kaolin | 67% | — | 67% | — |

The active ingredient mixture is thoroughly mixed with the adjuvants and the mixture is thoroughly ground in a suitable mill, affording wettable powders which can be diluted with water to give suspensions of the desired concentration.

| b) Emulsifiable concentrate | a) | b) | c) |
|---|---|---|---|
| Mixture of compounds of formulae I and II | 5% | 5% | 12% |
| octylphenolpolyethylene glycol ether (4-5 mol of ethylene oxide) | 3% | 3% | 3% |
| calcium dodecylbenzenesulfonate | 3% | 3% | 2% |
| castor oil polyglycol ether (36 mol of ethylene oxide) | 4% | 4% | 4% |
| cyclohexanone | 30% | 30% | 31% |
| xylene mixture | 50% | 35% | 35% |

Emulsions of any required concentration can be obtained from such concentrates by dilution with water.

| c) Dusts | a) | b) | c) | d) |
|---|---|---|---|---|
| Mixture of compounds of formulae I and II | 2% | 4% | 2% | 4% |
| talcum | 3% | 4% | 4% | 8% |
| kaolin | 95% | 92% | 94% | 88% |

Ready-for-use dusts are obtained by mixing the active ingredient mixture with the carrier and grinding the mixture in a suitable mill.

| d) Extruder granules | a) | b) | c) |
|---|---|---|---|
| Mixture of compounds of formulae I and II | 5% | 3% | 5% |
| sodium lignosulfonate | 2% | 2% | 2% |
| carboxymethylcellulose | 1% | 1% | 1% |
| kaolin | 87% | 87% | 77% |

The active ingredient mixture is mixed and ground with the adjuvants, and the mixture is moistened with water. The mixture is extruded and then dried in a stream of air.

| e) Coated granules | a) | b) |
|---|---|---|
| Mixture of compounds of formulae I and II | 1.5% | 3% |
| polyethylene glycol (mol. wt. 200) | 3% | 3% |
| kaolin | 94% | 89% |

The finely ground active ingredient mixture is uniformly applied, in a mixer, to the kaolin moistened with polyether glycol. Non-dusty coated granules are obtained in this manner.

| f) Suspension concentrate | a) | b) |
|---|---|---|
| Mixture of compounds of formulae I and II | 20% | 20% |
| ethylene glycol | 10% | 10% |
| nonylphenlpolyethylene glycol ether (15 mol of ethylene oxide) | 6% | 6% |
| sodium lignosulfonate | 10% | 10% |
| carboxymethylcellulose | 1% | 1% |
| 37% aqueous formaldehyde solution | 0.2% | 0.2% |
| silicon oil in the form of a 75% aqueous emulsion | 0.8% | 0.8% |
| water | 32% | 12% |

The finely ground active ingredient mixture is intimately mixed with the adjuvants, giving a suspension concentrate from which suspensions of any desired concentration can be obtained by dilution with water.

It is often more practical to formulate the compound of formula I and the co-component of formulae II-IX individually and then, just before they are used, to combine them in the desired ratio in the applicator in the form of a tank mixture in water.

What is claimed is:

1. A herbicidal composition comprising a sulfonylurea of formula I

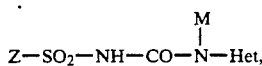

wherein

Z is a substituted phenyl radical;

M is hydrogen; or $C_1-C_4$alkyl; and

Het is a substituted five- or six-membered heterocycle having 2 or 3 nitrogen atoms, or an agrochemically acceptable salt thereof, and a synergistically effective amount of a 5,6,7,8-tetrahydro-1H,3H-(1,3,4)-thiadiazolo[3,4-a]pyridazine or 7,8-dihydro-1H,3H-(1,3,4)-thiadiazolo[3,4-a]pyridazine of the general formula II

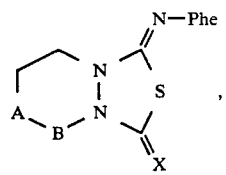

wherein

X is oxygen; or sulfur,

A-B is —CH₂—CH₂—; or —CH=CH—; and

Phe is a substituted phenyl radical.

2. A herbicidal composition according to claim 1, comprising a herbicidally active sulfonylurea of formula I

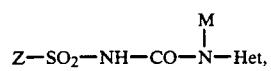

wherein

Z is a radical 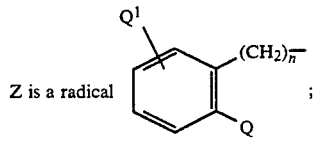 ;

Het is a radical 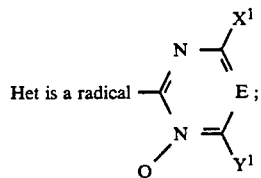

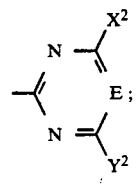

or

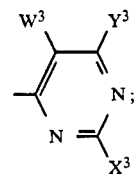

M is hydrogen; or $C_1-C_4$alkyl;

Q is halogen; nitro; $C_1-C_6$alkyl; $C_1-C_6$haloalkyl; $C_2-C_6$alkenyl; $C_2-C_6$haloalkenyl; $C_2-C_6$alkynyl; $C_3-C_6$haloalkynyl; —NH₂; —NH—($C_1-C_4$alkyl); —N($C_1-C_4$alkyl)₂; —SO₂N($C_1-C_4$alkyl)₂; —SO₂NH($C_1-C_4$alkyl); —COOR², —COOR'; —(-A)—R'; —(A)—R², phenyl; phenoxy; $C_1-C_5$alkylphenyl; halophenyl; or halophenoxy;

$Q^1$ is hydrogen; nitro; $C_1-C_4$alkyl; halogen; $C_1-C_4$alkoxy; $C_1-C_4$haloalkyl; N($C_1-C_4$alkyl)₂; $C_1-C_4$alkylamino; $C_1-C_4$haloalkylthio; $C_1-C_4$haloalkoxy; $C_1-C_4$alkoxy-$C_1-C_4$alkoxy; $C_2-C_4$alkenyl; $C_2-C_4$alkynyl; CN; or $C_2-C_4$haloalkenyl;

n is 0;

A is oxygen; sulfur; —SO—; —SO₂—; or —O—SO₂—;

$R^2$ is $C_1-C_5$alkyl; $C_2-C_6$alkenyl; $C_3-C_6$alkynyl; $C_1-C_5$haloalklyl; $C_1-C_4$alkoxy-$C_1-C_4$alkyl; $C_2-C_5$haloalkenyl; or $C_2-C_5$haloalkynyl;

R' is oxetan-3-yl; or thietan-3-yl;

E is N; or CH;

$X^1$, $X^2$, $X^3$ and $Y^1$, each independently of the others, is hydrogen; halogen; $C_1-C_4$haloalkoxy; $C_1-C_4$haloalkyl; $C_1-C_4$alkoxy; $C_1-C_4$alkyl; cyclopropyl; dimethylamino; methylamino; ethylamino; amino; $C_1-C_4$alkoxy-$C_1-C_4$alkyl; $C_1-C_4$alkoxy-$C_1-C_4$alkoxy; $C_1-C_4$haloalkylthio; $C_1-C_4$alkylthio; or $C_1-C_4$-alkylthio-$C_1-C_4$alkyl;

$Y^2$ is hydrogen; halogen; $C_1-C_4$haloalkoxy; $C_1-C_4$haloalkyl; $C_1-C_4$alkoxy; $C_1-C_4$alkyl; dimethylamino; methylamino; ethylamino; amino; $C_1-C_4$alkoxy-$C_1-C_4$alkyl; cyclopropyl; dimethoxymethyl; diethoxyethyl;

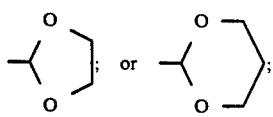

Y³ is C₁-C₄alkyl; C₁-C₄alkoxy; C₁-C₂haloalkyl; or C₁-C₂haloalkoxy;

W³ is hydrogen; C₁-C₄alkyl; C₁-C₄alkoxy; C₁-C₂haloalkyl; C₁-C₂haloalkoxy; C₁-C₄alkoxycarbonyl; halogen; cyano; nitro; C₁-C₄alkylthio; C₁-C₄alkylsulfinyl; or C₁-C₄alkylsulfonyl; or W³ and Y³ together are a C₂-C₄alkylene bridge; or a C₁-C₃alkylene bridge interrupted once by oxygen; with a synergistically effective amount of a 5,6,7,8-tetrahydro-1H,3H-(1,3,4)-thiadiazolo[3,4-a]pyridazine or 7,8-dihydro-1H,3H-(1,3,4)-thiadiazolo[3,4-a]pyridazine of formula II

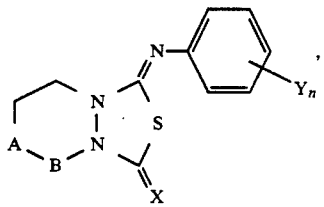

wherein

A—B is —CH₂—CH₂—; —CH=CH—;

each Y, independently of the others, is halogen; hydroxy; C₁-C₆alkyl; C₁-C₆alkoxy; C₁-C₆haloalkoxy; C₃-C₆alkenyloxy; C₂-C₆haloalkenyloxy; C₃-C₆alkynyloxy; phenoxy; C₅-C₆cycloalkyloxy; C₁-C₆alkoxycarbonyl-C₁-C₄alkoxy; C₁-C₆alkoxycarbonyl-C₂-C₄alkenyloxy; C₁-C₆alkylthiocarbonyl-C₁-C₄alkoxy; C₃-C₆alkynyloxycarbonyl-C₁-C₄alkoxy; benzyloxycarbonyl-C₁-C₄alkoxy; trifluoromethyl; benzyloxy; chlorobenzyloxy; C₁-C₆alkylbenzyloxy; C₂-C₆alkenyl; cyanoC₁-C₆alkyl; C₁-C₆alkylcarbamoyloxy; C₁-C₄alkoxy-C₁-C₄alkoyl; C₃-C₆alkynyloxy-C₁-C₄alkyl; C₃-C₆alkenyloxy-C₁-C₃alkyl; unsubstituted or halo-substituted C₅-C₆cycloalkylmethoxy; C₁-C₆alkoxy-C₁-C₄alkoxy; phenethyloxy, C₅-C₆cycloalkoxycarbonyl-C₁-C₄alkoxy; pyrrolidinocarbonyl; unsubstituted or C₁-C₆alkyl-substituted phenylcarbonyl; —CO—X⁵—R³;

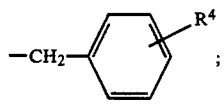

—S(O)ₚ—R⁵; —O—CH(R⁶)—CO—OR⁷;
—N=C(CH₃)—R⁸, —NHR⁹; —S—CH(R¹⁰)—CO—R¹¹; or —O—P(X⁵)(OC₂H₅)₂;

R³ is hydrogen; C₁-C₆alkyl; phenyl; C₅-C₆cycloalkyl; C₁-C₆alkoxy-C₁-C₄alkyl; C₁-C₆alkoxycarbonyl-C₁-C₄alkyl; or C₁-C₄alkoxy-C₁-C₄alkoxycarbonyl-C₁-C₄alkyl;

R⁴ is hydrogen; C₁-C₆alkoxy; C₁-C₄alkyl; or halogen;

R⁵ is C₁-C₆alkyl; C₂-C₆alkenyl; or C₂-C₆alkynyl;
P is 0 or 2;
R⁶ is hydrogen; or C₁-C₆alkyl;

R⁷ is hydrogen; C₁-C₆alkyl; C₁-C₆alkoxy-C₁-C₄alkyl; tetrahydrofuryl; C₁-C₄alkoxy-C₁-C₄alkoxy-C₁-C₄alkyl; C₁-C₆alkoxycarbonyl-C₁-C₄alkyl; or C₅-C₆cycloalkyl;

R⁸ is C₁-C₆alkyl; or phenyl;

R⁹ is C₁-C₆alkylcarbonyl; or C₁-C₆alkoxycarbonyl-C₁-C₄alkyl;

R¹⁰ is hydrogen; or C₁-C₆alkyl;

R¹¹ is C₁-C₆alkoxy; C₅-C₆cycloalkyloxy; 1-pyrrolidinyl; C₃-C₆alkenyloxy; C₃-C₆alkynyloxy; C₁-C₆alkylthio; C₁-C₆haloalkoxy; C₁-C₄alkoxycarbonyl-C₁-C₄alkoxy; α,α-dimethylbenzylamino; —OC₂H₄S(O)₂-(C₁-C₆alkyl); —OC₂H₄S-(C₁-C₆alkyl); —OC₂H₄S(O)₂-(phenyl); —OC₂H₄S-(phenyl);

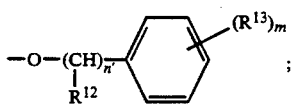

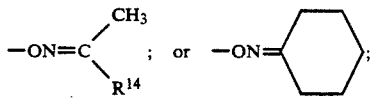

n' is 0; or 1;

R¹² is halogen; or C₁-C₄alkyl;

R¹³ is phenyl; benzyl; or methoxy-C₁-C₄alkyl;

R¹⁴ is styryl; cyano-C₁-C₄alkyl; tetrahydrofuran-2-yl, thienyl or pyridin-2-yl;

X is oxygen; or sulfur,

X⁵ is oxygen; or sulfur, m is 0; 1; 2; or 3;

and n is 0; 1; 2; or 3.

3. A composition according to claim 2, comprising a sulfonylurea formula I, wherein Het is the radical

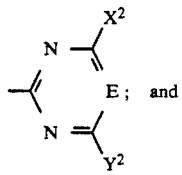

M is hydrogen; or C₁-C₄alkyl;

Q is halogen; nitro; C₁-C₆alkyl; C₁-C₆haloalkyl; C₂-C₆alkenyl; C₂-C₆haloalkenyl; C₂-C₆alkynyl; C₃-C₆haloalkynyl; —SO₂N(CH₃)₂; —COOR²; —COOR'; or —(A)—R²;

R² is C₁-C₅alkyl; C₂-C₅alkenyl; C₂-C₅alkynyl; C₁-C₅haloalkyl; C₁-C₄alkoxy-C₁-C₄alkyl; C₂-C₅haloalkenyl; or C₂-C₅haloalkynyl;

R' is oxetan-3-yl; or thietan-3-yl;

A is oxygen; sulfur; —SO₂—; or —O—SO₂—;

Q¹ is hydrogen; nitro; halogen; OCH₃; OCHF₂; CH₃; or SCH₃;

X² is C₁-C₄haloalkoxy; C₁-C₄haloalkyl; C₁-C₄alkoxy; C₁-C₄alkyl; halogen; SCH₃; cyclopropyl; dimethylamino; methylamino; or C₁-C₄alkoxy-C₁-C₄alkyl;

Y² is C₁-C₄haloalkoxy; C₁-C₄haloalkyl; C₁-C₄alkoxy; C₁-C₄alkyl; cyclopropyl; dimethylamino; methylamino; or C₁-C₄alkoxy-C₁-C₄alkyl; and E is CH; or N; or an agrochemically acceptable salt thereof.

4. A composition according to claim 3, comprising a sulfonylurea of formula Ia

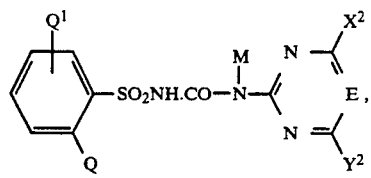

wherein

M is hydrogen; or $C_1$-$C_4$alkyl;

Q is halogen; nitro; $C_1$-$C_6$haloalkyl; $C_2$-$C_6$alkenyl; $C_2$-$C_6$haloalkenyl; $C_2$-$C_6$alkynyl; —$SO_2N(CH_3)_2$; —$COOR_2$; —COOR'; or —(A)—$R_2$;

A is oxygen; sulfur; or —$SO_2$—;

$R^2$ is $C_1$-$C_5$alkyl; $C_3$-$C_6$alkenyl; $C_3$-$C_6$alkynyl; $C_1$-$C_5$haloalkyl; $C_1$-$C_4$alkoxy-$C_1$-$C_4$alkyl; $C_2$-$C_5$haloalkenyl; or $C_2$-$C_5$haloalkynyl;

R' is oxetan-3-yl; or thietan-3-yl;

$Q^1$ is hydrogen; nitro; halogen; $OCH_3$; $OC_2$; $CH_3$; or $SCH_3$;

$X^2$ is $C_1$-$C_4$haloalkoxy; $C_1$-$C_4$haloalkyl; $C_1$-$C_4$alkoxy; $C_1$-$C_4$alkyl; halogen; $SCH_3$; cyclopropyl; dimethylamino; methylamino; or $C_1$-$C_4$alkoxy-$C_1$-$C_4$alkyl;

$Y^2$ is $C_1$-$C_4$haloalkoxy; $C_1$-$C_4$haloalkyl; $C_1$-$C_4$alkoxy; $C_1$-$C_4$alkyl; cyclopropyl; dimethylamino; methylamino; or $C_1$-$C_4$alkoxy-$C_1$-$C_4$alkyl; and E is CH; or N;

or an agrochemically acceptable salt thereof.

5. A composition according to claim 4, comprising a sulfonylurea of formula Ia, wherein M is hydrogen; or methyl;

Q is $C_1$-$C_6$haloalkyl; $C_2$-$C_6$haloalkenyl; —(A-)—$R^2$; —COOR'; or —$COOR_2$;

A is oxygen; or sulfur;

$R^2$ is $C_1$-$C_6$haloalkyl; $C_1$-$C_2$alkoxy-$C_1$-$C_3$alkyl; or $C_1$-$C_2$alkyl;

R' is oxetan-3-yl; or thietan-3-yl;

E is N; or CH;

$Q^1$ is hydrogen; and $X^2$ and $Y^2$, each independently of the other, is $C_1$-$C_4$alkyl; $C_1$-$C_4$haloalkoxy; halogen; or $C_1$-$C_4$alkoxy.

6. A composition according to claim 5, comprising a sulfonylurea of formula Ia, wherein Q is $C_1$-$C_6$fluoroalkyl; $C_2$-$C_6$fluoroalkenyl; or —(A-)—$R^2$, $R^2$ is $C_1$-$C_6$fluoroalkyl or $C_1$-$C_6$chloroalkyl;

E is N;

$Q^1$ is hydrogen; and $X^2$ and $Y^2$, each independently of the other, is methyl; or methoxy.

7. A composition according to claim 5, comprising a synergistically effective amount of a compound of formula II

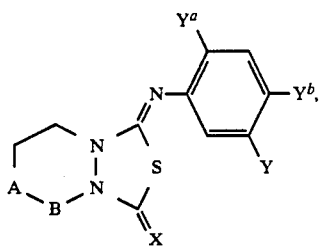

wherein

A-B is —$CH_2$—$CH_2$—; or —CH=CH—;

Y is hydroxy; $C_1$-$C_6$alkyl; $C_1$-$C_6$alkoxy; $C_1$-$C_6$haloalkoxy; $C_3$-$C_6$alkenyloxy; $C_2$-$C_6$haloalkenyloxy; $C_3$-$C_6$alkynyloxy; phenoxy; $C_5$-$C_6$Cycloalkyloxy; $C_1$-$C_6$alkoxycarbonyl-$C_1$-$C_4$alkoxy; $C_1$-$C_6$alkoxycarbonyl-$C_2$-$C_4$alkenyloxy; $C_1$-$C_6$alkylthiocarbonyl-$C_1$-$C_4$alkoxy; $C_3$-$C_6$alkynyloxycarbonyl-$C_1$-$C_4$alkoxy; benzyloxy $R^2$ is $C_1$-$C_5$alkyl; $C_3$-$C_6$alkenyl; $C_3$-$C_6$alkynyl; $C_1$-$C_5$haloalkyl; carbonyl-$C_1$-$C_4$alkoxy; trifluoromethyl; benzyloxy; chlorobenzyloxy; $C_1$-$C_6$alkylbenzyloxy; $C_2$-$C_6$alkenyl; cyano-$C_1$-$C_6$alkyl; $C_1$-$C_6$alkylcarbamoyloxy; $C_1$-$C_4$alkoxy-$C_1$-$C_4$alkyl; $C_3$-$C_6$alkynyloxy-$C_1$-$C_4$alkyl; $C_3$-$C_6$alkenyloxy-$C_1$-$C_4$alkyl; unsubstituted or halo-substituted $C_5$-$C_6$cycloalkylmethoxy; $C_1$-$C_6$alkoxy-$C_1$-$C_4$alkoxy; phenethyloxy; $C_5$-$C_6$Cycloalkoxycarbonyl-$C_1$-$C_4$alkoxy; pyrrolidinocarbonyl; unsubstituted or $C_1$-$C_6$alkyl-substituted phenylcarbonyl; —CO—$X^5$—$R^3$;

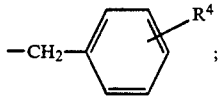

—$S(O)_p$—$R^5$;     —O—CH($R^6$)—CO—OR';
—N=C($CH_3$)—$R^8$;     —$NHR^9$;     —S—CH($R^{10}$)—CO—$R^{11}$; or —O—P($X^5$)($OC_2H_5$)$_2$;

$Y^a$ and $Y^b$, each independently of the other, is hydrogen; fluorine; chlorine; or bromine; and $R^3$ to $R^{11}$, X, $X^5$ and p are as defined above.

8. A composition according to claim 7, comprising a compound of formula II

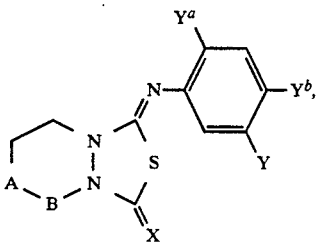

wherein

A-B is —$CH_2$—$CH_2$—; or —CH=CH—;

Y is $C_1$-$C_6$alkoxy; $C_1$-$C_6$haloalkoxy; $C_3$-$C_6$alkenyloxy; $C_2$-$C_6$haloalkenyloxy; $C_3$-$C_6$-alkynyloxy; $C_5$-$C_6$cycloalkyloxy; $C_1$-$C_6$alkoxycarbonyl-$C_1$-$C_4$alkoxy; $C_1$-$C_6$alkoxycarbonyl-$C_2$-$C_4$alkenyloxy; $C_1$-$C_6$alkylthiocarbonyl-$C_1$-$C_4$alkoxy; $C_3$-$C_6$alkynyloxycarbonyl-$C_1$-$C_4$alkoxy; cyano-$C_1$-$C_6$alkyl; $C_1$-$C_6$alkylcarbamoyloxy; $C_1$-$C_6$alkoxy-$C_1$-$C_4$alkoxy; phenoxy; benzyloxy; —S(O)$_p$-R$^5$; —O—CH(R$^6$)—CO—OR$^7$; —CO—X$^5$ —R$^3$; or —S—CH(R$^{10}$)—CO—R$^{11}$;

Y$^a$ is hydrogen; fluorine; or chlorine;

Y$^b$ is hydrogen; fluorine; chlorine; or bromine;

R$^3$ is hydrogen; C$_1$-C$_6$alkyl; phenyl; C$_5$-C$_6$cycloalkyl; C$_1$-C$_6$alkoxy-C$_1$-C$_4$alkyl; C$_1$-C$_6$alkoxycarbonyl-C$_1$-C$_4$alkyl; or C$_1$-C$_4$alkoxy-C$_1$-C$_4$alkoxycarbonyl-C$_1$-C$_4$alkyl;

R$^5$ is C$_1$-C$_6$alkyl; C$_3$-C$_6$alkenyl; or C$_3$-C$_6$alkynyl;

p is 0 or 2;

R$^6$ is hydrogen; or C$_1$-C$_6$alkyl;

R$^7$ is hydrogen; C$_1$-C$_6$alkyl; C$_1$-C$_6$alkoxy-C$_1$-C$_4$alkyl; tetrahydrofuryl; C$_1$-C$_4$alkoxy-C$_1$-C$_4$alkoxy-C$_1$-C$_4$alkyl; C$_1$-C$_6$alkoxycarbonyl-C$_1$-C$_4$alkyl; or C$_5$-C$_6$cycloalkyl;

R$^{10}$ is hydrogen; or C$_1$-C$_6$alkyl;

R$^{11}$ is C$_1$-C$_6$alkoxy; C$_2$-C$_6$cycloalkyloxy; 1-pyrrolidinyl; C$_3$-C$_6$alkenyloxy; C$_3$-C$_6$alkynyloxy; C$_1$-C$_6$alkylthio; C$_1$-C$_6$haloalkoxy; C$_1$-C$_4$alkoxycarbonyl-C$_1$-C$_4$alkoxy; α,α-dimethylbenzylamino; —OC$_2$H$_4$S(O)$_2$—(C$_1$-C$_6$alkyl); —OC$_2$H$_4$S—(C$_1$-C$_6$alkyl); —OC$_2$H$_4$S(O)$_2$-(phenyl); —OC$_2$H$_4$S-(phenyl);

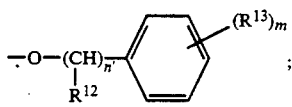

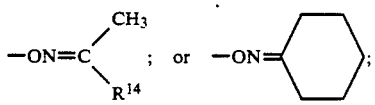

m is 0; 1; 2; or 3;

n is 0; or 1;

R$^{12}$ is halogen; or C$_1$-C$_4$alkyl;

R$^{13}$ is phenyl; benzyl; or methoxy-C$_1$-C$_4$alkyl;

R$^{14}$ is Styryl; cyano-C$_1$-C$_4$alkyl; tetrahydrofuran-2-yl, thienyl or pyridin-2-yl;

X is oxygen; or sulfur; and

X$^5$ is oxygen; or sulfur.

9. A composition according to claim 7, comprising a compound of formula IIa

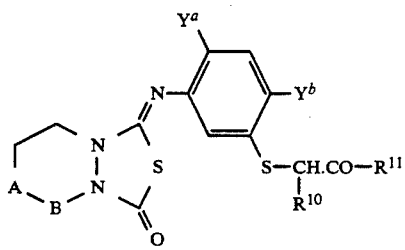

wherein

A-B, Y$^a$, Y$^b$, R$^{10}$ and R$^{11}$ are as defined above.

10. A composition according to claim 2, comprising a sulfonylurea of formula Ia

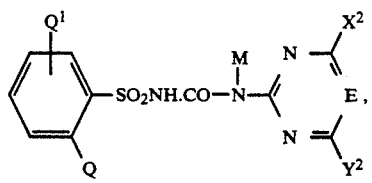

wherein

M is hydrogen;

Q is C$_1$-C$_6$haloalkyl; C$_2$-C$_6$haloalkenyl; or —(A-)—R$^2$;

A is oxygen; or sulfur;

R$^2$ is C$_1$-C$_6$haloalkyl;

E is N;

Q$^1$ is hydrogen; and

X$^2$ and Y$^2$, each independently of the other, is C$_1$-C$_4$alkyl; C$_1$-C$_4$alkoxy; or C$_1$-C$_4$haloalkoxy;

and a compound of formula IIa

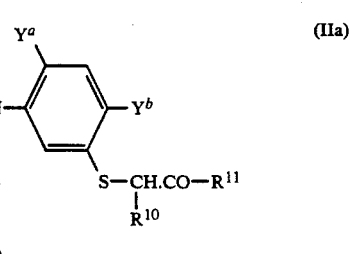

wherein

A-B is —CH$_2$—CH$_2$—;

Y$^a$ is hydrogen; or fluorine;

Y$^b$ is chlorine; or bromine;

R$^{10}$ is hydrogen; or C$_1$-C$_4$alkyl; and

R$^{11}$ is C$_1$-C$_4$alkoxy; C$_5$-C$_6$cycloalkyloxy; C$_3$-C$_6$alkenyloxy; C$_3$-C$_6$alkynyloxy; C$_1$-C$_4$alkylthio; or C$_1$-C$_4$alkoxycarbonyl-C$_1$-C$_4$alkoxy.

11. A composition according to claim 1, comprising N-[2-(2-chloroethoxy)phenylsulfonyl]-N'-(4-methoxy-6-methyl-1,3,5-triazin-2-yl)-urea as compound of formula I together with a synergistically effective amount of 3-[(4-chloro-2-fluoro-5-methoxycarbonylmethylthio)phenyl-imino]-5,6,7,8-tetrahydro-1H,3H-(1,3,4)-thiadiazolo[3,4-a]pyridazine as compound of formula II.

12. A method of controlling undesired dicot plant growth in a crop of useful cultivated plants which comprises the step of applying a herbicidally effective amount of a composition of claim 1 to the cultivated plants or the locus thereof.

13. The method of claim 12 wherein the cultivated plants are a cereal.

14. The method of claim 12 wherein the cultivated plants are maize.

15. The method of claim 12 wherein the cultivated plants are soybeans.

16. The method of claim 12 wherein the cultivated plants are rice.

* * * * *

UNITED STATES PATENT AND TRADEMARK OFFICE
CERTIFICATE OF CORRECTION

PATENT NO. : 5,310,722
DATED : May 10, 1994
INVENTOR(S) : Willy Maurer and Urs Hofer It is certified that error appears in the above-identified patent and that said Letters Patent is hereby corrected as shown below:

On the cover page, Item [73] should read:

-- Assignees: Ciba-Geigy Corporation, Ardsley, N. Y. and

KUMIAI CHEMICAL INDUSTRY CO., LTD., Tokyo, Japan --.

Signed and Sealed this

Thirteenth Day of September, 1994

Attest:

BRUCE LEHMAN

*Attesting Officer*  *Commissioner of Patents and Trademarks*